United States Patent
Wang et al.

(10) Patent No.: US 12,049,487 B2
(45) Date of Patent: Jul. 30, 2024

(54) UNIVERSAL CHIMERIC ANTIGEN RECEPTOR T-CELL PREPARATION TECHNIQUE

(71) Applicant: GRACELL BIOTECHNOLOGIES (SHANGHAI) CO., LTD., Shanghai (CN)

(72) Inventors: Xinxin Wang, Shanghai (CN); Zhongdong Shi, Shanghai (CN); Liping Liu, Shanghai (CN); Chunhui Yang, Shanghai (CN); Jing Sun, Shanghai (CN); Songbai Cai, Shanghai (CN); Wei Cao, Shanghai (CN)

(73) Assignee: GRACELL BIOTECHNOLOGIES (SHANGHAI) CO., LTD., Shanghai (CN)

( * ) Notice: Subject to any disclaimer, the term of this patent is extended or adjusted under 35 U.S.C. 154(b) by 983 days.

(21) Appl. No.: 16/645,290

(22) PCT Filed: Sep. 6, 2018

(86) PCT No.: PCT/CN2018/104418
§ 371 (c)(1),
(2) Date: Mar. 6, 2020

(87) PCT Pub. No.: WO2019/047899
PCT Pub. Date: Mar. 14, 2019

(65) Prior Publication Data
US 2023/0265154 A1 Aug. 24, 2023

(30) Foreign Application Priority Data
Sep. 6, 2017 (CN) .......................... 201710797952.4

(51) Int. Cl.
*C07K 14/725* (2006.01)
*C07K 16/28* (2006.01)
*C12N 5/0783* (2010.01)

(52) U.S. Cl.
CPC ...... *C07K 14/7051* (2013.01); *C07K 16/2803* (2013.01); *C12N 5/0636* (2013.01); *C07K 2317/53* (2013.01); *C07K 2317/622* (2013.01); *C07K 2319/03* (2013.01); *C12N 2310/20* (2017.05); *C12N 2510/00* (2013.01)

(58) Field of Classification Search
CPC .......................... C07K 14/7051; C12N 5/0636
See application file for complete search history.

(56) References Cited

U.S. PATENT DOCUMENTS

2014/0349402 A1  11/2014  Cooper et al.
2018/0362975 A1* 12/2018  Chen ..................... C12N 15/113
2020/0407693 A1* 12/2020  Hotta ..................... C12N 15/11

FOREIGN PATENT DOCUMENTS

| WO | 2013/074916 A1 | 5/2013 |
| WO | 2016044605 A1 | 3/2016 |
| WO | 2016/069282 A1 | 5/2016 |
| WO | 2016183041 A1 | 11/2016 |
| WO | 2017093969 A1 | 6/2017 |

OTHER PUBLICATIONS

Romagne et al., Blood. 2009; 114:2667-2677 (Year: 2009).*
English translation of International Search Report and Written Opinion for Application No. PCT/CN2018/104418 dated Dec. 13, 2018 (8 pages).
Torikai et al., "Toward Eliminating HLA Class I Expression to Generate Universal Cells from Allogeneic Donors," Blood, 2013, 122(8):1341-1349.
Iu et al., "CRISPR-Cas9-Mediated Multiplex Gene Editing in CAR-T cells," Cell Res., 2017, 27(1):154-157.
Chinese Patent Office First Office Action for application 201710797952. 4, dated Jul. 27, 2021, translation, 7 pages.
Chinese Patent Office Rejection for application 201710797952.4, dated Jun. 20, 2022, 6 pages with English abstract.
Chinese Patent Office Second Office Action for application 201710797952.4, dated Jan. 14, 2022, translation, 7 pages.
European Patent Office. Communication pursuant to Article 94(3) EPC for application 18854819.2, dated Aug. 5, 2022, 4 pages.
European Patent Office. Communication pursuant to Article 94(3) EPC for application 18854819.2, dated Oct. 19, 2021, 5 pages.
European Patent Office. Extended European Search Report for application 18854819.2, dated Oct. 26, 2020, 10 pages.
Torikai, H., et al. "Genetic editing of HLA expression in hematopoietic stem cells to broaden their human application." Scientific reports 6.1 (2016): 21757.

* cited by examiner

*Primary Examiner* — Jessica H Roark
(74) *Attorney, Agent, or Firm* — Michael Best & Friedrich LLP

(57) ABSTRACT

Provided are a universal chimeric antigen receptor (CAR) T cell and preparation method and application thereof. The binding of the cell HLA-A/HLA-B to the TCR is inhibited; the TCR gene expression is silenced; the invention may be used for allogeneic tumor treatment and does not cause GVHD and HVG reaction during allogeneic infusion, and thus improves the survival and antineoplastic effect of allogeneic CAR-T cells in the recipient.

10 Claims, 4 Drawing Sheets
Specification includes a Sequence Listing.

UNIVERSAL CHIMERIC ANTIGEN RECEPTOR T-CELL PREPARATION TECHNIQUE

CROSS-REFERENCE TO RELATED APPLICATION(S)

This application is a U.S. national stage filing under 35 U.S.C. § 371 of International Patent Application No. PCT/CN2018/104418, filed on Sep. 6, 2018, which claims priority to and the benefit of Chinese Patent Application No. 201710797952.4, filed on Sep. 6, 2017, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 25,174 bytes ASCII (Text) file named "P2020-0304Sequence_20Dec.2023.txt," created on Dec. 20, 2023.

TECHNICAL FIELD

The present invention relates to the field of immune cell therapy, in particular to a universal chimeric antigen receptor T cell as well as preparation method and application thereof.

BACKGROUND TECHNIQUE

Cellular immunotherapy is an emerging and highly effective tumor treatment model, and is a novel autoimmunology treatment mothed for cancer. It is a method comprising steps of in vitro culture and amplification of immune cells obtained from a patient, and transfusing the cells back to the patient to stimulate using biotechnology and biological agents, and enhancing the body's autoimmune function, thereby achieving the purpose of treating tumors.

Chimeric antigen receptors (CARs) are consisted of an extracellular antigen recognition domain which is usually a scFv (single-chain variable fragments), a transmembrane domain, and an intracellular co-stimulatory signal domain. The extracellular region of CARs can recognize a specific antigen, and then transduce the signal through the intracellular domain, causing the activation and proliferation of T cells, cytolysis toxicity, and secretion of cytokines, thereby eliminating target cells.

CAR-T cells have shown unprecedented efficacy in the treatment of hematological malignancies. For example, complete remission (CR) can reach 90% for the treatment of advanced relapsed refractory acute lymphoblastic leukemia (ALL), and CR is over 50% for chronic lymphocytic leukemia (CLL) and some B-cell lymphomas. In addition, CAR-T cells also show great potential in the treatment of solid tumors.

In traditional CAR-T cell therapy, firstly T cells from autologous patient (or heterologous donor) are isolated, activated and genetically modified to generate CAR-T cells, and then injected into the same patient. The probability of graft versus host disease in the way is extremely low, and antigens are recognized by T cells in a non-MHC-restricted manner. However, this type of treatment is severely constrained by the individual condition of the patient, and the time and costs of isolating and modifying cells are also very high. Therefore, further research in the field is still needed to develop a universal CAR-T cell that can be prepared on a large scale with uniform and stable quality and can be used at any time for any patient.

SUMMARY OF THE INVENTION

It is an object of the present invention to provide a universal chimeric antigen receptor T cell as well as preparation method and application thereof.

In a first aspect of the invention, it provides a universal chimeric antigen receptor T cell (CAR-T cell) with the following characteristics:
   (a) the CAR-T cell expresses a chimeric antigen receptor CAR, and the CAR targets a marker of tumor cells; and
   (b) the binding of HLA-A and/or HLA-B of the CAR-T cell to TCR (T cell receptor) is inhibited.

In another preferred embodiment, the endogenous $\beta 2$ m gene is normally expressed in the universal CAR-T cell.

In another preferred embodiment, the "gene is normally expressed" means that the $\beta 2$ m gene expression level of the universal CAR-T cell is the same as or substantially the same as the $\beta 2$ m gene expression level of a normal T cell. Typically, the ratio (E1/E0) of $\beta 2$ m gene expression level E1 of the universal CAR-T cell to $\beta 2$ m gene expression level E0 of a normal T cell is 0.5-2.0, preferably 0.6-1.5, and more preferably 0.8-1.2.

In another preferred embodiment, the endogenous $\beta 2$ m polypeptide exerts its normal function in the universal CAR-T cell.

In another preferred embodiment, the "binding of HLA-A and/or HLA-B to TCR is inhibited" means that HLA-A does not bind or substantially does not bind to TCR, and/or HLA-B does not bind or substantially does not bind to TCR.

In another preferred embodiment, the "HLA-A substantially does not bind to TCR" means that the ratio of binding amount A1 of HLA-A of the CAR-T cell to TCR to the binding amount A0 of HLA-A of a normal T cell to TCR, i.e. A1/A0, is $\leq 0.05$, preferably $\leq 0.03$, more preferably $\leq 0.02$, more preferably $\leq 0.01$, and most preferably 0.

In another preferred embodiment, the "HLA-B substantially does not bind to TCR" means that the ratio of binding amount B1 of HLA-B of the CAR-T cell to TCR to the binding amount B0 of HLA-B of a normal T cell to TCR, i.e. B1/B0, is $\leq 0.05$, preferably $\leq 0.03$, more preferably $\leq 0.02$, more preferably $\leq 0.01$, and most preferably 0.

In another preferred embodiment, the TCR is derived from a receptor T cell.

In another preferred embodiment, the HLA-I gene expression of the CAR-T cell is silenced, so that the binding of HLA-A and/or HLA-B to TCR (T cell receptor) is inhibited.

In another preferred embodiment, the $\beta 2$ m gene expression of the CAR-T cell is silenced, so that the binding of HLA-A and/or HLA-B to TCR (T cell receptor) is inhibited.

In another preferred embodiment, the $\beta 2$ m is $\beta 2$ m in HLA-I.

In another preferred embodiment, the HLA-I comprises HLA-A, HLA-B, and/or HLA-C.

In another preferred embodiment, the CAR-T cell expresses an exogenous ligand fragment or antibody fragment of NK cell inhibitory receptor (killer-cell immunoglobulin-like receptor, KIR).

In another preferred embodiment, the ligand fragment of the inhibitory receptor comprises a full-length HLA-C or an HLA-C fragment.

In another preferred embodiment, the antibody fragment of the inhibitory receptor is scFv of a KIR antibody, preferably 1-7F9VL and/or 1-7F9VH.

In another preferred embodiment, the amino acid sequence of the 1-7F9VL is as shown in SEQ ID NO: 3.

In another preferred embodiment, the amino acid sequence of the 1-7F9VH is as shown in SEQ ID NO: 4.

In another preferred embodiment, the HLA-C fragment comprises α1 and α2 of HLA-C.

In another preferred embodiment, the HLA-A and/or HLA-B gene expression of the CAR-T cell is silenced, so that the binding of HLA-A and/or HLA-B to TCR (T cell receptor) is inhibited.

In another preferred embodiment, the HLA-C gene expression of the CAR-T cell is not affected.

In another preferred embodiment, the TCR gene expression of the CAR-T cell is silenced.

In another preferred embodiment, the "gene expression is silenced" means that the silenced gene is not expressed or has low expression.

In another preferred embodiment, the "low expression" means that the ratio of the silenced gene expression level G1 of the CAR-T cell to the corresponding gene expression level G0 of a normal T cell, i.e. G1/G0, is ≤0.5, preferably ≤0.3, more preferably ≤0.2, more preferably ≤0.1, and most preferably 0.

In another preferred embodiment, the structure of the CAR is shown in formula I as below:

L1-scFv-H1-TM1-C-CD3ζ-K      (I)

wherein,
each "-" is independently a linker peptide or a peptide bond;
L1 is an optional signal peptide sequence;
scFv is an antigen binding domain;
H1 is an optional hinge region;
TM1 is a transmembrane domain;
C is a co-stimulatory signaling molecule;
CD3ζ is a cytoplasmic signaling sequence derived from CD3ζ;
K is an optional KIR ligand element.

In another preferred embodiment, the KIR ligand element comprises a ligand fragment or an antibody fragment of an inhibitory receptor.

In another preferred embodiment, the ligand fragment of the inhibitory receptor comprises a full-length HLA-C or an HLA-C fragment.

In another preferred embodiment, the antibody fragment of the inhibitory receptor is scFv of a KIR antibody, preferably 1-7F9VL and/or 1-7F9VH.

In another preferred embodiment, the structure of the KIR ligand element is shown in formula II as below:

L2-R-H2-TM2      (II)

wherein,
each "-" is independently a linker or a peptide bond;
L2 is an optional signal peptide sequence;
R is a ligand fragment or an antibody fragment of an inhibitory receptor;
H2 is an optional hinge region;
TM2 is an optional transmembrane domain.

In another preferred embodiment, the H2 is a hinge region derived from CD8.

In another preferred embodiment, the TM2 is a transmembrane domain derived from CD8.

In another preferred embodiment, the KIR ligand element K and CD3ζ are linked by T2A.

In another preferred embodiment, the L1 is a signal peptide of a protein selected from the group consisting of CD8, GM-CSF, CD4, CD137, and a combination thereof.

In another preferred embodiment, the L1 is GM-CSF.

In another preferred embodiment, the scFv is an antibody single-chain variable region sequence targeting a tumor antigen.

In another preferred embodiment, the scFv is an antibody single-chain variable region sequence targeting an antigen selected from the group consisting of CD19, CD20, CD22, CD123, CD47, CD138, CD33, CD30, mesothelin, EGFR, GPC3, BCMA, ErbB2, NKG2D ligand, LMP1, EpCAM, VEGFR-1, Lewis-Y, ROR1, Claudin 18.2, and a combination thereof.

In another preferred embodiment, the scFv is an antibody single-chain variable region sequence targeting CD19.

In another preferred embodiment, the scFv is FMC63, and the sequence is as shown in positions 67-801 of SEQ ID NO: 1.

In another preferred embodiment, the H1 is a hinge region of a protein selected from the group consisting of CD8, CD28, CD137, and a combination thereof.

In another preferred embodiment, the H1 is a hinge region derived from CD28.

In another preferred embodiment, the TM1 is a transmembrane region of a protein selected from the group consisting of CD28, CD38, CD45, CD4, CD5, CD8, CD9, CD16, CD22, CD33, CD37, CD64, CD80, CD86, CD134, CD137, CD154, and a combination thereof.

In another preferred embodiment, the TM1 comprises a transmembrane region derived from CD28.

In another preferred embodiment, the C is a co-stimulatory signaling molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, and a combination thereof.

In another preferred embodiment, the C comprises a co-stimulatory signaling molecule derived from CD28.

In another preferred embodiment, the structure of the CAR is L-FMC63-CD28-CD3ζ.

In another preferred embodiment, the sequence of the CAR is as shown in SEQ ID NO: 2.

In another preferred embodiment, the CAR-T cell is used for the treatment of allogeneic tumors.

In another preferred embodiment, the CAR-T cell does not induce GVHD and HVG responses during allogeneic treatment.

In a second aspect of the invention, it provides a method for preparing the CAR-T cell according to the first aspect of the invention, comprising the following steps:
(A) providing a T cell to be modified; and
(B) modifying the T cell to express the CAR, and inhibiting the binding of HLA-A and/or HLA-B of the CAR-T cell to TCR, thereby obtaining the CAR-T cell according to the first aspect of the invention.

In another preferred embodiment, in step (B), HLA-A and HLA-B genes are knocked out using a gene editing system. Preferably, the gene editing system comprises CRISPR-Cas9 system, zinc finger protein system, or TALEN system.

In another preferred embodiment, the CRISPR-Cas9 system comprises gRNA and Cas9 protein.

In another preferred embodiment, the gRNA comprises a second gRNA targeting HLA-a and a third gRNA targeting HLA-b.

In another preferred embodiment, any of the above gRNA comprises (a) tracRNA and crRNA; (b) sgRNA, or a combination thereof.

In another preferred embodiment, the step (B) comprises (B1) transferring a first expression cassette expressing the CAR into the T cell; and (B2) transferring a second expression cassette for silencing β2 m into the T cell;

wherein the order of the steps (B1) and (B2) is random.

In another preferred embodiment, the step (B) further comprises step (B3) transferring a third expression cassette for silencing TCR gene into the T cell;

wherein the order of the steps (B1), (B2) and (B3) is random.

In another preferred embodiment, the step (B) further comprises step (B4) transferring a fourth expression cassette expressing an exogenous ligand fragment or antibody fragment of NK cell inhibitory receptor into the T cell;

wherein the order of the steps (B1), (B2), (B3) and (B4) is random.

In another preferred embodiment, the "order is random" means that any two steps can be performed in turn, simultaneously, or in reverse order.

In another preferred embodiment, the step (B) comprises (B1) transferring a first expression cassette expressing the CAR into the T cell; and (B2') transferring a fifth expression cassette for silencing HLA-A and/or HLA-B into the T cell;

wherein the order of the steps (B1) and (B2) is random.

In another preferred embodiment, the step (B) further comprises step (B3) transferring a third expression cassette for silencing TCR gene into the T cell;

wherein the order of the steps (B1), (B2') and (B3) is random.

In another preferred embodiment, when the T cell to be modified in step (A) has expressed a certain CAR, the step (B) comprises (B2') transferring a fifth expression cassette for silencing HLA-A and/or HLA-B into the T cell; and (B3) transferring a third expression cassette for silencing TCR gene into the T cell;

wherein the step (B2') may be performed before, after, simultaneously, or alternatively with step (B3).

In another preferred embodiment, the expression cassettes are located on the same or different vectors.

In another preferred embodiment, the first expression cassette and the fourth expression cassette are located on the same vector.

In another preferred embodiment, the vector is a virus vector.

In another preferred embodiment, the vector is selected from the group consisting of DNA, RNA, plasmid, lentiviral vector, adenoviral vector, retroviral vector, transposon, other gene transfer systems, and a combination thereof.

In another preferred embodiment, the second expression cassette comprises CRISPR/Cas9 (first sgRNA and Cas9), antisense RNA, or a combination thereof. In another preferred embodiment, the first sgRNA targets β2 m.

In another preferred embodiment, the sequence of the first sgRNA is as shown in SEQ ID NO: 5 or 6.

In another preferred embodiment, the antisense RNA comprises miRNA, siRNA, shRNA, inhibitory mRNA, or dsRNA.

In another preferred embodiment, the fifth expression cassette comprises CRISPR/Cas9 (second sgRNA and Cas9), antisense RNA, or a combination thereof.

In another preferred embodiment, the second sgRNA targets HLA-a and/or HLA-b.

In another preferred embodiment, the third expression cassette comprises CRISPR/Cas9 (second sgRNA and Cas9), antisense RNA, or a combination thereof.

In another preferred embodiment, the third sgRNA targets TCR gene.

In another preferred embodiment, the sequence of the third sgRNA is as shown in SEQ ID NO: 3 or 4.

In a third aspect of the invention, it provides a preparation comprising the CAR-T cell according to the first aspect of the invention, and a pharmaceutically acceptable carrier, diluent or excipient.

In another preferred embodiment, the preparation is a liquid preparation.

In another preferred embodiment, the preparation is an injection.

In another preferred embodiment, the concentration of the CAR-T cells in the preparation is $1 \times 10^3 – 1 \times 10^8$ cells/ml, preferably $1 \times 10^4 – 1 \times 10^7$ cells/ml.

In a fourth aspect of the invention, it provides a use of the CAR-T cell according to the first aspect of the invention for the preparation of a medicament or a preparation for preventing and/or treating cancer or tumor.

In another preferred embodiment, the medicament or preparation is used for preventing and/or treating a cancer or tumor that is allogeneic with the CAR-T cell.

In another preferred embodiment, the tumor is selected from the group consisting of a hematological tumor, a solid tumor, and a combination thereof.

In another preferred embodiment, the blood tumor is selected from the group consisting of acute myeloid leukemia (AML), multiple myeloma (MM), chronic lymphocytic leukemia (CLL), acute lymphoblastic leukemia (ALL), diffuse large B cell lymphoma (DLBCL), and a combination thereof.

In another preferred embodiment, the solid tumor is selected from the group consisting of gastric cancer, peritoneal metastasis of gastric cancer, liver cancer, leukemia, renal cancer, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, and a combination thereof.

In a fifth aspect of the invention, it provides a kit for preparing the CAR-T cell according to the first aspect of the invention, wherein the kit comprises a container and following components located in the container:

(1) a first nucleic acid sequence comprising a first expression cassette for expressing the CAR;
(2) a second nucleic acid sequence comprising a second expression cassette or a first gRNA for silencing β2 m, or a fifth expression cassette or a second gRNA and/or a third gRNA for silencing HLA-A and/or HLA-B.

In another preferred embodiment, the kit further comprises: (3) a third nucleic acid sequence comprising a third expression cassette or a third sgRNA for silencing the TCR gene.

In another preferred embodiment, the kit further comprises: (4) a fourth nucleic acid sequence comprising a fourth expression cassette for expressing an exogenous ligand fragment or antibody fragment of NK cell inhibitory receptor.

In another preferred embodiment, the first, second, third and fourth nucleic acid sequences are independent or connected.

In another preferred embodiment, the first, second, third and fourth nucleic acid sequences are located in the same or different containers.

In another preferred embodiment, any two, three or four of the first, second, third and fourth nucleic acid sequences are located in the same expression vector.

In another preferred embodiment, the kit further comprises: (4) a fifth nucleic acid sequence comprising a sixth expression cassette for expressing Cas9 protein; or a Cas9 protein.

In a sixth aspect of the invention, it provides a use of the CAR-T cell according to the first aspect of the invention for the prevention and/or treatment of an allogeneic cancer or tumor.

It is to be understood that the various technical features of the present invention mentioned above and the various technical features specifically described hereinafter (as in the Examples) may be combined with each other within the scope of the present invention to constitute a new or preferred technical solution, which will not be repeated one by one herein, due to space limitations.

DESCRIPTION OF DRAWINGS

FIG. 12a shows the proportion of CAR+ cells and the expression of HLA-A by FACS quantitative analysis; wherein Mock refers to the universal CAR-T cell without HLA-A/B and β2M knockout, and NT refers to normal T cell that has not been genetically edited and does not express CAR. FIG. 12b shows the killing of Hela-CD19 cells by AB dKO and β2M KO CAR-T cells relative to normal universal CAR-T cells by RTCA analysis. FIG. 12c shows the killing of different cells by NK92 cells, wherein the X-axis represents the effector target ratio (E:T), the data is mean +/−SD, and * is P<0.01. FIG. 12d shows the protection ratio of AB dKO CAR-T relative to β2M KO CAR-T against the killing of NK92 cells.

MODES FOR CARRYING OUT THE PRESENT INVENTION

Figure 1:
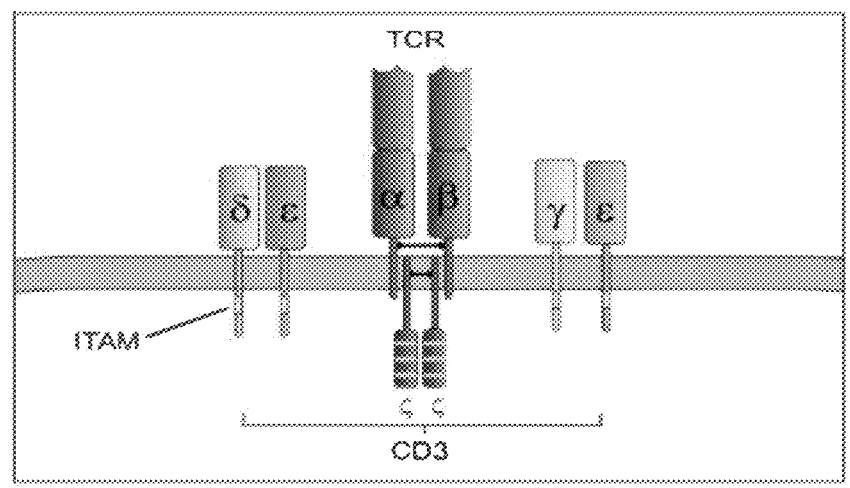
FIG. 1 shows the structure of TCR.

After extensive and intensive studies, the inventors unexpectedly obtained a universal chimeric antigen receptor T cell as well as preparation method and application thereof for the first time. Specifically, the invention provides a universal CAR-T cell expressing a chimeric antigen receptor CAR, and the binding of HLA-A and/or HLA-B of the cell to TCR is inhibited, and the TCR gene expression in the cell is silenced. Experiments show that the universal CAR-T cells of the invention can be used for the treatment of allogeneic tumors, and would not induce GVHD and HVG responses during allogeneic infusion, thus improving the survival of allogeneic CAR-T cells in the receptor and the anti-tumor effect thereof. The present invention has been completed on the basis of this.

Specifically, the chimeric antigen receptor T cell of the invention is a cell that can treat tumors and does not induce GVHD and HVG responses during allogeneic treatment. To be precise, it is a T cell expressing a chimeric antigen receptor and the TCR expression in the cell is knocked out by gene editing technology, so that the normal cell of the receptor will not be killed by TCR recognition during allogeneic infusion, that is, it will not bring GVHD response. At the same time, to avoid host versus graft (HVG) response and improve the survival of allogeneic CAR-T cells in the receptor and the anti-tumor effect thereof, the following methods are performed:

(1) the key binding sites (positions 222-229) to CD8 molecules in the α3 region of the HLA-I molecules are point mutated, so that the ability to activate T cells after HLA-TCR binding is reduced to avoid the attack of receptor T cells and HVG response;

(2) the α3 region in HLA-I molecules is gene silenced, so that HLA molecules do not bind to CD8 molecules, and the ability to activate T cells after HLA-TCR binding is reduced to avoid the attack of receptor T cells and HVG response;

(3) the expression of β2 m in HLA-I molecules is knocked out by gene editing, so that the HLA-I molecule expression is silenced, and at the same time exogenous ligand fragment or antibody fragment of NK cell inhibitory receptor (killer-cell immunoglobulin-like receptor, KIR) is high expressed;

(4) the expression of HLA-A/HLA-B is knocked out or knocked down, so that the receptor TCR does not recognize CAR-T cells to avoid HVG;

(5) the sites recognized by TCR in the α1 and α2 domains of HLA-I molecules are mutated, while the sites binding to KIR are retained, so that the HLA-I is not recognized by the receptor TCR but can bind to KIR receptor in NK cells to avoid HVG response.

Term

To make the disclosure easier to understand, some terms are firstly defined. As used in this application, unless expressly stated otherwise herein, each of the following terms shall have the meanings given below. Other definitions are set forth throughout the application.

The term "about" may refer to a value or composition within an acceptable error range for a particular value or composition as determined by those skilled in the art, which will depend in part on how the value or composition is measured or determined.

The term "administering" refers to the physical introduction of a product of the invention into a subject using any one of various methods and delivery systems known to those skilled in the art, including intravenous, intramuscular, subcutaneous, intraperitoneal, spinal or other parenteral administration, such as by injection or infusion.

The term "antibody" (Ab) may include, but is not limited to, an immunoglobulin that specifically binds an antigen and contains at least two heavy (H) chains and two light (L) chains linked by disulfide bonds, or an antigen binding parts thereof. Each H chain contains a heavy chain variable region (abbreviated herein as VH) and a heavy chain constant region. The heavy chain constant region contains three constant domains, CH1, CH2, and CH3. Each light chain contains a light chain variable region (abbreviated herein as VL) and a light chain constant region. The light chain constant region contains a constant domain CL. The VH and VL regions can be further subdivided into hypervariable regions called complementarity determining regions (CDR), which are interspersed within more conservative regions called framework regions (FR). Each VH and VL contains three CDRs and four FRs, which are arranged from amino terminal to carboxy terminal in the following order: FR1, CDR1, FR2, CDR2, FR3, CDR3, FR4. The variable regions of the heavy and light chains contain a binding domain that interacts with an antigen.

TCR/MHC Complex (T Cell Receptor, TCR)

T cell receptor (TCR) is a characteristic marker on the surface of all T cells. It binds to CD3 with non-covalent bonds to form a TCR-CD3 complex. The role of TCR is to recognize antigens and activate T cells to exert killing effects. TCR is a heterodimer consisted of two different peptide chains. TCR is divided into two categories: TCR1 and TCR2. TCR1 is consisted of two chains of γ and δ, and TCR2 is composed of two chains of α and β. In peripheral blood, 90%-95% of T cells express TCR2. Each peptide chain can be divided into variable region (V region), constant region (C region), transmembrane region and cytoplasmic region. It is characterized by a short cytoplasmic region. The structure of TCR is shown in FIG. 1.

The TCR molecule belongs to the immunoglobulin superfamily, and its antigen specificity exists in the V region. Each V region (Vα, Vβ) has three hypervariable regions CDR1, CDR2, and CDR3, among which CDR3 has the largest variation, which directly determines the TCR antigen binding specificity. When TCR recognizes the MHC-antigen-peptide complex, CDR1 and CDR2 recognize and bind to the side of the antigen binding cleft of MHC molecules, while CDR3 directly binds to the antigen peptide.

Major histocompatibility complex (MHC) is a general term for all biocompatibility complex antigens (MHC molecule), representing molecules encoded by the MHC gene family (MHC class I, class II, class III). MHC is located on the cell surface, and the products encoded by different mammalian MHC gene have different names. Human MHC is commonly referred to as HLA (human leucocyte antigen, HLA), that is, human leukocyte antigen. MHC gene is located in the short arm of human chromosome 6. The gene is highly polymorphic.

Figure 2:
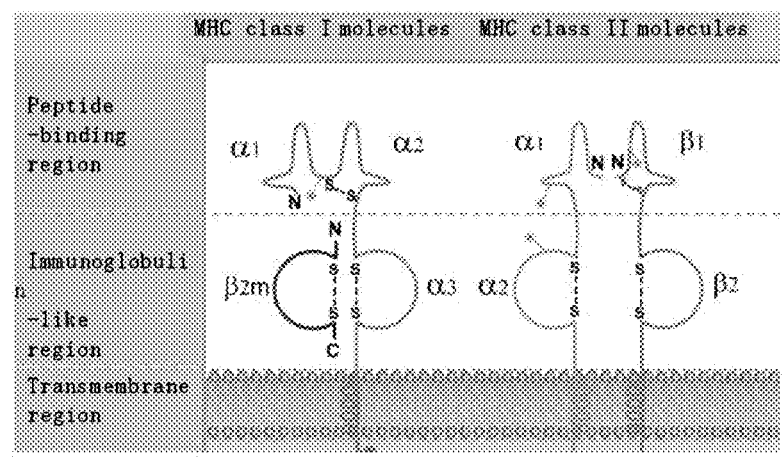
FIG. 2 shows the structure of MHC molecules.

MHC molecules are involved in antigen recognition during immune response. There are two main types, MHC class I molecules and MHC class II molecules. MHC class I molecules are distributed on the surface of almost all cells and participate in the internal antigen presentation process. MHC class II molecules are mainly distributed on the surface of antigen-presenting cells (CD4+ T cells, macrophages, B lymphocytes, etc.) and participate in the exogenous antigen presentation. MHC class I molecules are consisted of a heavy chain (α chain, divided into three domains of α1, α2, and α3) and a light chain β microglobulin. MHC class II molecules are consisted of two heavy chains of α chain and β chain, and each has two domains: α1, α2, B1, and B2. The structure of MHC molecules is shown in FIG. 2.

Figure 3:
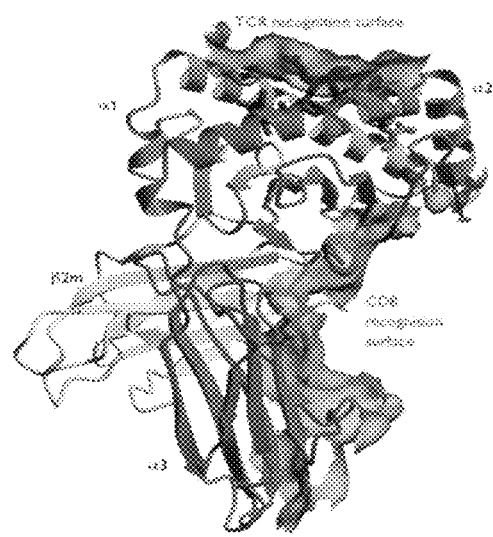
FIG. 3 shows the three-dimensional structure of MHC class I molecules.

FIG. 3 shows the three-dimensional structure of MHC class I molecules. When allogeneic MHC complex molecules are presented to T cells by APC, the allogeneic MHC complexes are specifically recognized by TCR (as shown in the figure). TCRCDR1, CDR2 binds to α1 and α2 of HLA in MHC molecules, and TCR CDR3 specifically binds to the antigen peptide. The CD8 molecules in the TCR complex are recognized by α3 region of the HLA molecules. The combinations cooperate to activate T cells, allowing T cells to rapidly proliferate, and ultimately specifically kill allogeneic cells. Therefore, during allotransplantation, it is necessary to reduce or block the recognition of recipient TCR and donor MHC complex to prevent the transplanted cells from being cleared by the T cells in the recipient. Therefore, on one hand, the TCR receptor of CART cells needs to be knocked out to prevent normal cells in the recipient from being killed during allogeneic infusion. On the other hand, the MHC molecules on the surface of CART can be knocked out to avoid attack of the recipient T cells. This is also the current mainstream approach, but once the MHC molecules on the surface of CART cells are not expressed, the NK cells in the recipient are not inhibited by MHC and will be activated to perform killing function, affecting the survival and therapeutic effects of CAR-T cells. Therefore, how to regulate the expression of MHC molecules so that allogeneic CART cells are not attacked by either T cells or NK cells is particularly important.

NK Cell Inhibitory Receptor (Killer-Cell Immunoglobulin-Like Receptor, KIR)

NK cells are bone marrow-derived lymphocytes. Unlike T cells, NK cells perform non-specific killing function and do not rely on MHC restriction. NK cells induce apoptosis of target cells mainly through two methods: granule exocytosis and death receptor, and can also be directly activated to exert antibody-dependent cell-mediated cytotoxicity (ADCC effect).

The activation of NK cells is mainly regulated by the balance between inhibitory receptors and activating receptors. Normal cells in the body will not be attacked by NK cells, because they express their own MHC class I molecules on the surface, which can bind to inhibitory receptors on the surface of NK cells, thereby inhibiting the activation of NK cells.

The inhibitory receptors that bind to MHCI are KIR, heterodimer NKG2A/CD94, and leukocyte Ig-like receptor (LIR). Classic HLAI molecules (HLA-A, -B, -C) are ligands of KIR and LIR.

The KIRs family is located on chromosome 19q13.4 and belongs to the Ig superfamily. It has two (KIR2D) or three (KIR3D) Ig domains in the extracellular region and is further typed according to the length of the cytoplasmic tail. The one with longer intracellular fragment is KIR2DL and KIRDL, and the one with shorter intracellular fragment is KIR2DS and KIR3DS. The long-tailed KIRs are linked to immunoreceptor tyrosine-based inhibitory motif (ITIM). KIRs specifically recognize MHC-i alleles, HLA-A, -B, and -C. HLA-C is a major class I molecular ligand that binds to inhibitory receptors. HLA-C is divided into two groups according to different amino acid residues at positions 77 and 80 of its alpha helix. HLA-Cw1, Cw3, Cw7, and Cw8 are in the first group, and the amino acid residues at positions 77 and 80 are serine and aspartic acid, respectively, which can be recognized by the inhibitory receptors KIR2DL2, KIR2DL3 and the activating receptors KIR2DS2, KIR2DS3. The second group of HLA-C alleles comprises HLA-Cw2, Cw4, Cw5 and Cw6, and the amino acid residues at positions 77 and 80 of the alpha helix are aspartic acid and lysine, which can be recognized by the inhibitory receptor KIR2DL1 and the activating receptor KIR2DS1.

Figure 4:
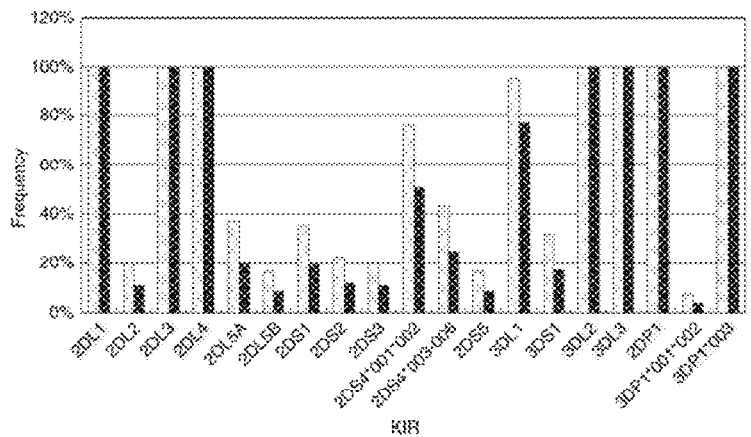
FIG. 4 shows the distribution frequency of KIR receptors in the northern Han Chinese.

Statistics show that the specific receptor molecules KIR2DL1 and KIR2DL3 of the HLA-C molecule are expressed in all population of Han Chinese (FIG. 4). Therefore, after all MHC-I molecules in allogeneic CART cells are knocked out, HLA-C molecules can be expressed to inhibit the activity of the recipient NK cells, avoid being killed by NK, and prolong the survival time in allogeneic body.

Figure 5:
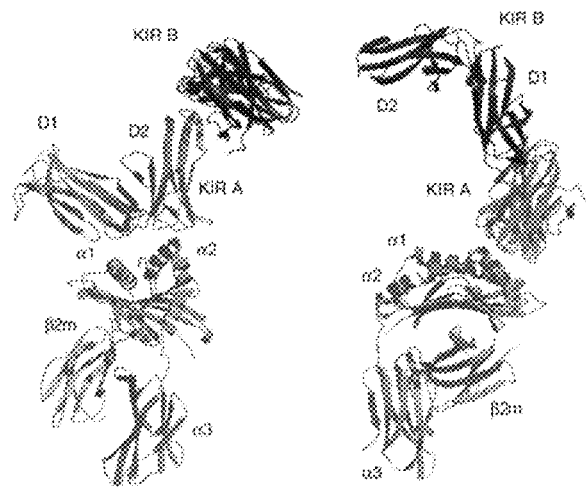
FIG. 5 shows the specific recognition of KIRs and HLA-C molecules.

FIG. 5 shows the specific recognition of KIRs and HLA-C molecules. Similar to TCR/HLA recognition, D1 and D2 of KIR molecules are recognized by α1 and α2 of HLA molecules, respectively.

Figure 6:
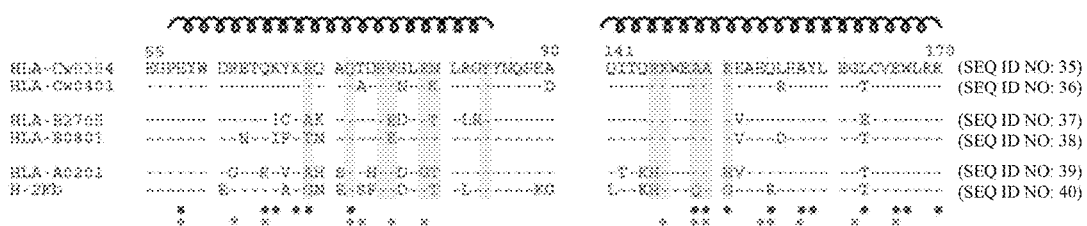
FIG. 6 shows the binding of KIR (SEQ ID NOS: 32-34) and TCR to different sites in HLA molecules (SEQ ID NOS: 35-40), respectively.

The binding sites of KIR to HLA-C are relatively conserved, as shown by the yellow highlight in FIG. 6 and there are 11 conserved sequences among the 12 binding sites. The positions marked by the red dot in FIG. 6 shows 16 binding sites of TCR and HLA-A, among which only 8 sites are conservative and the other 8 are variable. At the same time, it can be seen that KIR and TCR bind to different sites of HLA molecules. Therefore, the sites specifically recognized by TCR in the HLA site can be mutated, while the sites recognized by KIR are retained. Therefore, on the one hand, it is not recognized by TCR to avoid the attack of T cells, and on the other one hand, it can bind to KIR receptors to inhibit the activity of NK cells and avoid the attack of NK receptors. These prolong the survival time of donor cells in the body, and better exert the curative effect.

Chimeric Antigen Receptor (CAR)

The chimeric antigen receptor (CAR) of the invention comprises an extracellular domain, a transmembrane domain, and an intracellular domain. The extracellular domain comprises a target-specific binding element (also known as an antigen binding domain). The intracellular domain includes a co-stimulatory signaling region and a ζ chain. The co-stimulatory signaling region refers to a part of the intracellular domain that includes a co-stimulatory molecule. The co-stimulatory molecule is a cell surface molecule required for efficient response of lymphocytes to antigens, rather than an antigen receptor or its ligand.

The design of CARs has gone through the following process. The first generation CAR has only one intracellular signal component, CD3ζ or FcγRI molecule. Because there is only one activation domain in the cell, it can only cause transient T cell proliferation and less cytokine secretion. It does not provide long-term T cell proliferation signals and sustained antitumor effects in vivo, so it has not achieved good clinical effects. The second generation CAR introduced a costimulatory molecule based on the original structure, such as CD28, 4-1BB, OX40, and ICOS. Compared with the first generation CAR, the function has been greatly improved, and the sustainability of CAR-T cells and the ability to kill tumor cells are further enhanced. Based on the second generation CARs, some new immunostimulatory molecules such as CD27 and CD134 were linked in series to develop the third and fourth generation CARs.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

When the CAR of the present invention is expressed in T cell, antigen recognition can be performed based on antigen binding specificity. When the CAR binds to its associated antigen, it affects tumor cell, causing tumor cell to fail to grow, to death or to be affected otherwise, causing the patient's tumor burden to shrink or eliminate. The antigen binding domain is preferably fused to the intracellular domain from one or more of the co-stimulatory molecule and the & chain. Preferably, the antigen binding domain is fused with an intracellular domain of a combination of a CD28 signaling domain and a CD3ζ signaling domain.

As used herein, the "antigen binding domain" and "single-chain antibody fragment" refer to a Fab fragment, a Fab' fragment, a F(ab') 2 fragment, or a single Fv fragment that has antigen-binding activity. The Fv antibody contains the heavy chain variable region and the light chain variable region of the antibody, but has no constant region. And the Fv antibody has the smallest antibody fragment with all antigen-binding sites. Generally, Fv antibodies also include a polypeptide linker between the VH and VL domains, and can form the structure required for antigen binding. The antigen binding domain is usually a scFv (single-chain variable fragment). The size of scFv is typically ⅙ of a complete antibody. The single-chain antibody is preferably an amino acid chain sequence encoded by a nucleotide chain. As a preferred mode of the invention, the scFv comprises an antibody that specifically recognizes an antigen highly expressed by tumors, preferably a single-chain antibody.

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

CAR-T Cells

As used herein, the terms "CAR-T cell", "CAR-T", and "CAR-T cell of the invention" refer to the universal CAR-T cell according to the first aspect of the invention. The CAR-T cells expresses a chimeric antigen receptor CAR targeting tumor cell markers. Besides, the binding of HLA-A and/or HLA-B to TCR (T cell receptor) is inhibited.

As for the CAR-T cell of the invention, the TCR expression in the cell is knocked out by gene editing technology, so that the normal cells of the receptor will not be killed by TCR recognition during allogeneic infusion, that is, it will not bring GVHD response. At the same time, β2M is silenced, or HLA-A and/or HLA-B regions are silenced, preferably HLA-A and HLA-B regions are silenced simultaneously, so that the binding of HLA-A and/or HLA-B to TCR is inhibited. Besides, the cell also expresses an exogenous ligand fragment or antibody fragment of NK cell inhibitory receptor to avoid host versus graft (HVG) response and improve the survival of allogeneic CAR-T cells in the receptor and the anti-tumor effect thereof.

Gene Silencing Method

CRISPR/Cas9, RNA interference technology, TALENs (transcription activator-like (TAL) effector nucleases), and Zinc finger nucleases (ZFNs) are the commonly used methods for gene silencing. At present, CRISPR/Cas9 has the best application prospect and effect.

The CRISPR (clustered regularly interspersed short palindromic repeats)/Cas (CRISPR-associated) system is a natural immune system peculiar to prokaryotes, which is used to resist the attack of viruses or exogenous plasmids. The type II CRISPR/Cas system, as a RNA directly mediated genome editing tool, has been successfully applied in many eukaryotes and prokaryotes. The development of the CRISPR/Cas9 system has completely changed people's ability to edit DNA sequences and regulate the expression level of target genes, thus providing a powerful tool for accurate genome editing of organisms. The simplified CRISPR/Cas9 system consists of two parts: the Cas9 protein and sgRNA. Its working principle is that the sgRNA forms a Cas9-sgRNA complex with Cas9 protein through its own Cas9 handle. The sequence of the base complementary pairing region of the sgRNA in the Cas9-sgRNA complex and the target sequence of the target gene are paired according to the principle of base complementary pairing. Cas9 uses its own endonuclease activity to cleave the target DNA sequence. Compared with traditional genome editing technologies, the CRISPR/Cas9 system has several significant advantages: ease of use, simplicity, low cost, programmability, and the ability to edit multiple genes simultaneously.

Vector

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The present invention also provides vectors in which the expression cassette of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression cassette or nucleic acid sequence of the invention is typically and operably linked to a promoter, and incorporated into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In a preferred embodiment of the invention, the vector is a lentiviral vector.

Preparation

The invention provides a preparation comprising the CAR-T cell according to the first aspect of the invention, and a pharmaceutically acceptable carrier, diluent or excipient. In one embodiment, the preparation is a liquid preparation. Preferably, the preparation is an injection. Preferably, the concentration of the CAR-T cells in the preparation is $1\times10^3$–$1\times10^8$ cells/ml, more preferably $1\times10^4$–$1\times10^7$ cells/ml.

In one embodiment, the preparation may comprises buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The preparation of the invention is preferably formulated for intravenous administration.

Therapeutic Application

The invention comprises therapeutic applications using cells (e.g., T cells) transduced with a lentiviral vector (LV) encoding the expression cassette of the invention. The transduced T cells can target tumor cell markers and can be used for allogeneic tumor treatment, which can be prepared on a large scale with uniform and stable quality and can be used at any time for any patient.

Thus, the present invention also provides a method for stimulating a T cell-mediated immune response to a target cell population or tissue in a mammal comprising the step of administering to the mammal a CAR-T cell of the invention.

In one embodiment, the invention comprises a class of cell therapies in which the modified universal CAR-T cell of the invention is administered directly to a patient in need. As for the CAR-T cell of the invention, the TCR expression in the cell is knocked out by gene editing technology, so that the normal cells of the receptor will not be killed by TCR recognition during allogeneic infusion, that is, it will not bring GVHD response. At the same time, β2M is silenced, or HLA-A and/or HLA-B regions are silenced, so that the binding of HLA-A and/or HLA-B to TCR is inhibited. Besides, the cell also expresses an exogenous ligand fragment or antibody fragment of NK cell inhibitory receptor to avoid host versus graft (HVG) response and improve the survival of allogeneic CAR-T cells in the receptor and the anti-tumor effect thereof. In addition, one CAR-T can treat all cancers that express the antigen. Unlike antibody therapies, CAR-T cells are able to replicate in vivo resulting in long-term persistence that can lead to sustained tumor control In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-CD19 CAR-T cell elicits an immune response specific against cells expressing CD19.

Although the data disclosed herein specifically disclose lentiviral vector comprising scFv, hinge and transmembrane domain, and 4-1BB/CD28 and CD3ζg signaling domains, the invention should be construed to include any number of variations for each of the components of the construct as described elsewhere herein.

Cancers that may be treated include tumors that are unvascularized or largely unvascularized, and tumors that are vascularized. Cancers may include non-solid tumors (such as hematological tumors, for example, leukemias and lymphomas) or solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells (autologous or allogeneic), ii) introducing a nucleic acid encoding a CAR to the cells, and/or iii) cryopreservation of the cells.

Ex vivo procedures are well known in the art and are discussed more fully below. Briefly, cells (autologous or allogeneic) are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The present invention provides methods for treating tumors comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. In general, $1 \times 10^6$ to $1 \times 10^{10}$ of the modified T cells of the invention (e.g., CAR-T cells) can be applied to patients by means of, for example, intravenous infusion each treatment or each course of treatment.

The main advantages of the present invention are:
(A) The universal CAR-T cell of the invention can be used in allogeneic tumor treatment.
(b) The universal CAR-T cell of the invention does not cause GVHD and HVG responses during allogeneic infusion.
(c) The universal CAR-T cell of the invention can be prepared on a large scale with uniform and stable quality, and can be used at any time for any patient.
(d) Compared with other types of CAR-T cells, the universal CAR-T cells of the invention can significantly avoid being killed by the immune system (especially NK cells) of the recipient (or the host).

The present invention will be further illustrated below with reference to the specific examples. It is to be understood that these examples are for illustrative purposes only and are not intended to limit the scope of the invention. The experimental methods with no specific conditions described in the following examples are generally performed under the conventional conditions, or according to the manufacturer's instructions. Percentages and parts are by weight unless otherwise stated.

Example 1 Structural Design of CAR

CAR19 is taken as an example to construct CAR. In the structure of CAR19, a second generation CD19 CAR is used, comprising a scFv from FMC63, a hinge and transmembrane region from CD28, and CD28 and CD3ζ intracellular region. The structure is shown as below:

The DNA sequence of CAR19 is as follows (SEQ ID NO: 1):

```
   1 atgcttctcc tggtgacaag ccttctgctc tgtgagttac cacacccagc attcctcctg 61 atcccagaca tccagatgac acagactaca tcctccctgt ctgcctctct gggagacaga 121 gtcaccatca gttgcagggc aagtcaggac attagtaaat atttaaattg gtatcagcag 181 aaaccagatg gaactgttaa actcctgatc taccatacat caagattaca ctcaggagtc 241 ccatcaaggt tcagtggcag tgggtctgga acagattatt ctctcaccat tagcaacctg 301 gagcaagaag atattgccac ttactttgc caacagggta atacgcttcc gtacacgttc 361 ggaggggggga ctaagttgga ataacaggc tccacctctg gatccggcaa gcccggatct 421 ggcgagggat ccaccaaggg cgaggtgaaa ctgcaggagt caggacctgg cctggtggcg 481 ccctcacaga gcctgtccgt cacatgcact gtctcagggg tctcattacc cgactatggt 541 gtaagctgga ttcgccagcc tccacgaaag ggtctggagt ggctgggagt aatatggggt 601 agtgaaacca catactataa ttcagctctc aaatccagac tgaccatcat caaggacaac 661 tccaagagcc aagttttctt aaaaatgaac agtctgcaaa ctgatgacac agccatttac 721 tactgtgcca acattatta ctacggtggt agctatgcta tggactactg gggtcaagga 781 acctcagtca ccgtctcctc agcggccgca attgaagtta tgtatcctcc tccttaccta 841 gacaatgaga gagcaatgg aaccattatc catgtgaaag ggaaacacct ttgtccaagt 901 cccctatttc ccggaccttc taagcccttt tgggtgctgg tggtggttgg gggagtcctg 961 gcttgctata gcttgctagt aacagtggcc tttattattt tctgggtgag gagtaagagg 1021 agcaggctcc tgcacagtga ctacatgaac atgactcccc gccgccccgg gcccacccgc 1081 aagcattacc agccctatgc cccaccacgc gacttcgcag cctatcgctc cagagtgaag 1141 ttcagcagga gcgcagacgc cccgcgtac cagcagggca gaaccagct ctataacgag 1201 ctcaatctag gacgaagaga ggagtacgat gttttggaca agagacgtgg ccgggaccct
```

```
1261 gagatggggg gaaagccgag aaggaagaac cctcaggaag gcctgtacaa tgaactgcag 1321 aaagataaga tggcggaggc ctacagtgag attgggatga aaggcgagcg ccggaggggc 1381 aaggggcacg atggccttta ccagggtctc agtacagcca ccaaggacac ctacgacgcc 1441 cttcacatgc aggccctgcc ccctcgctaa
```

The amino acid sequence of CAR19 is as follows (SEQ ID NO: 2):

```
  1 mlllvtslll celphpafll ipdiqmtqtt sslsaslgdr vtiscrasqd
    iskylnwyqq
 61 kpdgtvklli yhtsrlhsgv psrfsgsgsg tdysltisnl eqediatyfc
    qqgntlpytf
121 gggtkleitg stsgsgkpgs gegstkgevk lqesgpglva
    psqslsvtet vsgvalpdyg
181 vswirqpprk glewlgviwg settyynsal ksrltiikdn
    sksqvflkmn slqtddtaiy
241 ycakhyyygg syamdywgqg tsvtvssaaa ievmypppyl
    dneksngtii hvkgkhlcps
301 plfpgpskpf wvlvvvggvl acysllvtva fiifwvrskr
    srllhsdymn mtprrpgptr
361 khyqpyappr dfaayrsrvk fsrsadapay qqgqnqlyne lnl-
    grreeyd vldkrrgrdp
421 emggkprrkn pqeglynelq kdkmaeayse igmkgerrrg
    kghdglyqgl statkdtyda
481 lhmqalppr
```

Example 2 Construction of CAR19-HLA-Cw1 (Abbreviated Hereinafter as 19.C1) Structure In the HLA-Cw1 molecule, the α1 and α2 structural sequences are followed by a CD8 hinge and transmembrane region, which is then integrated behind the CAR19 molecule and connected by T2A. They are constructed into the lentiviral vector framework, referred to as 19.C1.1. The structure is as follows:

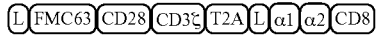

Alternatively, the scFv sequence of the KIR antibody is followed by a CD8 hinge and a transmembrane region, which is then integrated behind the CAR19 molecule connected by T2A. They are constructed into the lentiviral vector framework, referred to as 19.C1.2. The structure is as follows:

Amino acid sequence of 1-7F9VL (SEQ ID NO: 3):

```
EIVLTQSPVTLSLSPGERATLSCRASQSVSSYLAWYQQKPGQAPRLLIYD

ASNRATGIPARFSGSGSGTDFTLTISSLEPEDFAVYYCQQRSNWMYTFGQ

GTKLEIKRT
```

Amino acid sequence of 1-7F9VH (SEQ ID NO: 4):

```
QVQLVQSGAEVKKPGSSVKVSCKASGGTFSFYAISWVRQAPGQGLEW

MGGFIPIFGAANYAQKFQGRVTITADESTSTAYMELSSLRSDDTAVY

YCARIPSGSYYYDYDMDVWGQGTTVTVSS
```

Example 3 Construction of Lentiviral Vector

CD19 CAR was cloned into the FUW lentiviral vector framework and placed downstream of the EFIα promoter to form Fuw-EFIα-CD19CAR. Three plasmids Fuw-EFIα-CD19CAR, pMD2.G and psPAX2 (addgene) were transferred into 293T (ATCC, CRL-3216) using Lipofectamine2000 to prepare a lentiviral expression vector. Virus supernatants were collected on the second and third day, and the virus was obtained by ultracentrifugation for enrichment (Merck Millipore).

Similarly, 19.C1 CAR was cloned into the FUW lentiviral vector framework and placed downstream of the EFIα promoter to form Fuw-EFIα-19.C1 CAR. Three plasmids Fuw-EFIα-19.C1 CAR, pMD2.G, and pspax2 (addgene) were transfected into 293T (ATCC, CRL-3216) using Lipofectamine2000 to prepare a lentiviral expression vector. Virus supernatants were collected on the second and third day, and the virus was obtained by ultracentrifugation for enrichment (Merck Millipore).

Example 4 Construction of CRISPR-Cas9 System and Screening of gRNA 1) construction of CRISPR-Cas9 system The purpose of this example is to firstly screen out high-efficiency gRNAs for knocking out TCR/β2M/HLA-A/B. gRNA consists of a crRNA that matches a specific target and a tracrRNA with fixed sequence. The sequence of tracrRNA is:

```
                                        (SEQ ID NO: 5)
GTTTTAGAGCTAGAAATAGCAAGTTAAAATAAGGCTAGTCCGTTATC

AACTTGAAAAAGTGGCACCGAGTCGGTGCTTTT.
```

The crRNA was designed based on the target sequence and assessed for off-target risk. The designed gRNA was prepared by artificial synthesis. Cas9 protein was purchased from Genscript and IDT.

During gene editing, gRNA and Cas9 protein were firstly co-incubated at 37° C. or room temperature for 15 minutes to form ribonucleoprotein (RNP). RNP was transfected into cells by Lonza 4D nuclear transfection (Nucleofector).

The gene editing efficiency or gene knockout efficiency of the designed sgRNA was analyzed by flow cytometry (FACS) and T7EI test (see González, Zhu, Shi, et al., Cell Stem Cell. 2014. doi: 10.1016/j.stem.2014.05.018) and/or TIDE analysis. The results showed that the knockout efficiency using two sgRNAs together was more efficient than that of single sgRNA. In the invention, two sgRNAs and Cas9 plasmids are electrotransformed together.

2) Efficient crRNA screening (1) TCR knockout

TCR is consisted of two chains, α and β. TCR gene knockout is achieved by designing a TRAC locus that targets the conserved region of the TCR a chain.

The sequences of the selected crRNAs are as follows:

```
                                              (SEQ ID NO: 6)
    Seq 1: TGGATTTAGAGTCTCTCAGC (SEQ ID NO: 7)
    Seq 2: TTCGGAACCCAATCACTGAC (SEQ ID NO: 8)
    Seq 3: AAGTTCCTGTGATGTCAAGC (SEQ ID NO: 9)
    Seq 4: TCAGGGTTCTGGATATCTGT (SEQ ID NO: 10)
    Seq 5: CTGGAGGGCCCTGAGCAGAG (SEQ ID NO: 11)
    Seq 6: GAGCAGCAGGCAGGTTAGGC
```

Figure 7:
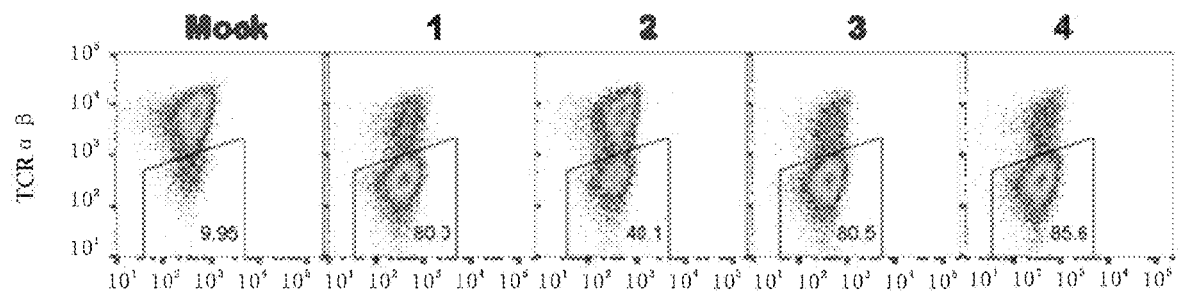
FIG. 7 shows the results of gRNA knockout efficiency of four TRACs by FACS analysis.

The results are shown in FIG. 7. FACS results showed that the knockout efficiency of gRNA-#1, -#3 and -#4 was better, which could all reach more than 70%, wherein gRNA-#4 is the most efficient. Therefore, gRNA-#4 is preferred as the gRNA for TCR knockout of the universal CAR-T cells according to the invention.

(2) β2 m knockout

MHC class I molecule is consisted of a heavy chain (α chain, divided into three domains of α1, α2, and α3) and a light chain β microglobulin. When β2 m is knocked out, a chain cannot be transferred to the membrane surface alone, achieving the effect of HLA molecule knockout.

The sequences of selected crRNA targeting β2 m are as follows:

```
                                              (SEQ ID NO: 12)
    β2m-Seq 1: CGTGAGTAAACCTGAATCTT (SEQ ID NO: 13)
    β2m-Seq 2: TATAAGTGGAGGCGTCGCGC (SEQ ID NO: 14)
    β2m-Seq 3: GGCCGAGATGTCTCGCTCCG (SEQ ID NO: 15)
    β2m-Seq 4: AAGTCAACTTCAATGTCGGA (SEQ ID NO: 16)
    β2m-Seq 5: ACTCACGCTGGATAGCCTCC (SEQ ID NO: 17)
    β2m-Seq 6: GGCCACGGAGCGAGACATCT (SEQ ID NO: 18)
    β2m-Seq 7: CGCGAGCACAGCTAAGGCCA (SEQ ID NO: 19)
    β2m-Seq 8: GAGTAGCGCGAGCACAGCTA
```

Figure 8:
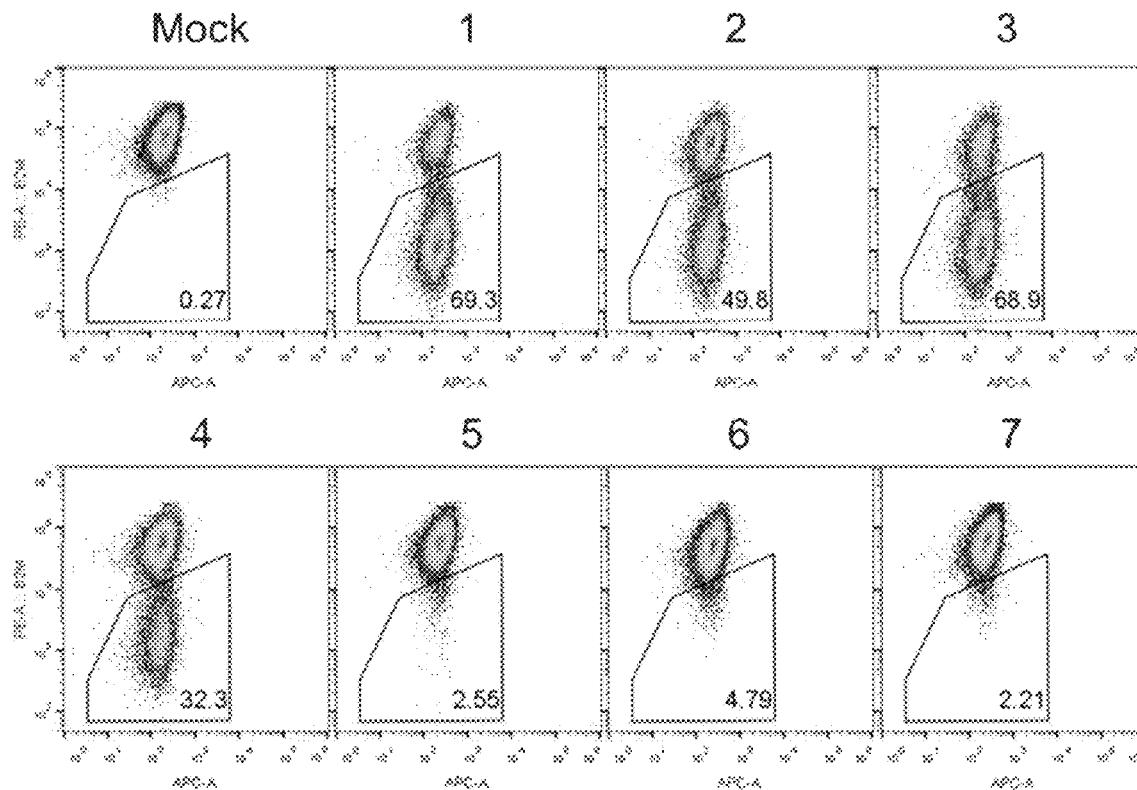
FIG. 8 shows the results of knockout efficiency of β2M gRNA by FACS analysis.

The β2M knockout efficiency of 7 gRNAs is shown in FIG. 8. Among them, #1 and #3 perform best and the β2M knockout efficiency can be close to 70%. Therefore #1 and #3 are the preferred two gRNAs for knocking out β2M.

(3) HLA-A/B knockout

1) The sequences of HLA-A and B crRNA are as follows:

HLA-A:

```
                                              (SEQ ID NO: 20)
    crRNA1: CCCTCCTCCTGCTACTCTCG (SEQ ID NO: 21)
    crRNA2: GCGCCCGCGGCTCCATCCTC (SEQ ID NO: 22)
    crRNA3: CCAGGGCCCCCGAGAGTAGC (SEQ ID NO: 23)
    crRNA4: CACTCGGTCAGTCTGTGACT (SEQ ID NO: 24)
    crRNA5: GATAATGTATGGCTGCGACG (SEQ ID NO: 25)
    crRNA6: ACAGACTGACCGAGTGGACC
```

HLA-B:

```
                                              (SEQ ID NO: 26)
    crRNA-B1: GGAGGTGTAGAAATACCTCA (SEQ ID NO: 27)
    crRNA-B2: ATTTCTACACCTCCGTGTCC (SEQ ID NO: 28)
    crRNA-B3: TGGACGACACCCAGTTCGTG (SEQ ID NO: 29)
    crRNA-B4: AGCAGCAGGAGGACGGTTCG (SEQ ID NO: 30)
    crRNA-B5: CGCTGTCGAACCTCACGAAC (SEQ ID NO: 31)
    crRNA-B6: GAGCATGTACGGCTGCGACG
```

(4) Screening results of HLA-A and B crRNA

Figure 9:
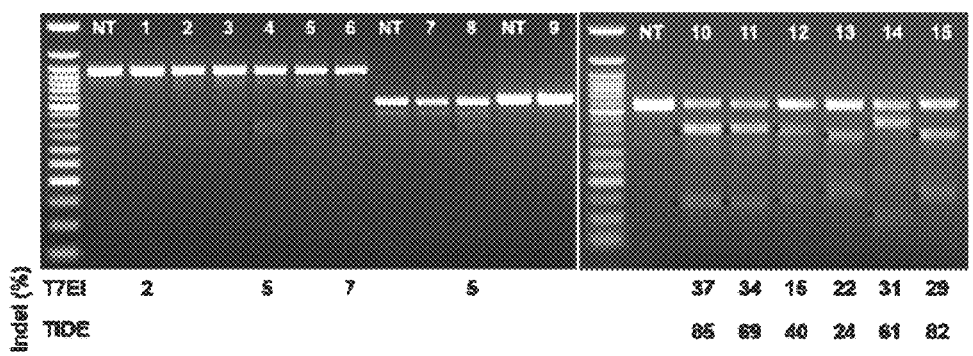
FIG. 9 shows the results of HLA-A gene editing efficiency of different gRNAs by T7EI and TIDE analysis.
Figure 10:
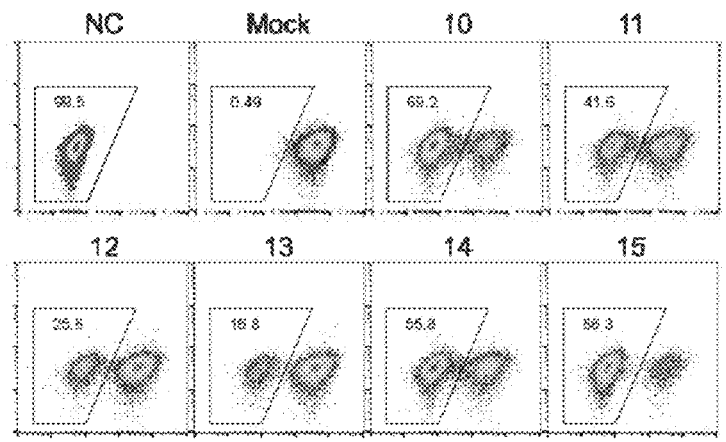
FIG. 10 shows the results of HLA-A gene knockout efficiency of different gRNAs by FACS analysis.

Through T7EI, TIDE, and FACS analysis (FIGS. 9 and 10), four high-efficiency gRNAs targeting HLA-A of #10, #11, #14, and #15 (that is, corresponding to crRNA1 to crRNA4) are obtained. The best two gRNAs were used as the gRNA for the subsequent knock-out of HLA-A.

Figure 11:
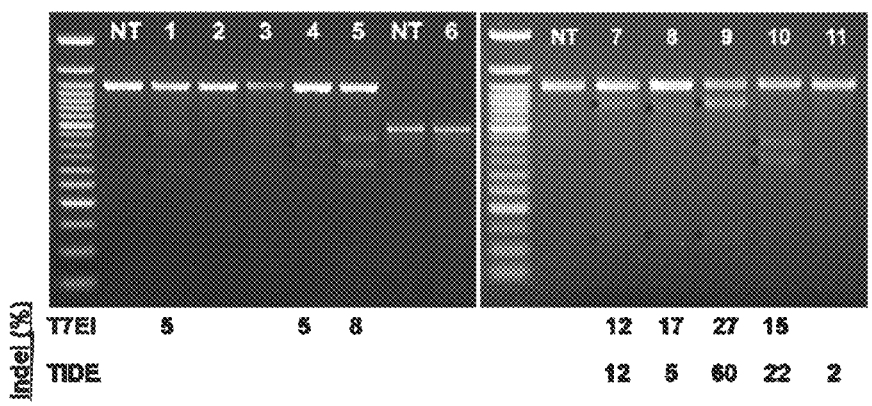
FIG. 11 shows the results of HLA-B gene editing efficiency of different gRNAs by T7EI and TIDE analysis.

In FIG. 11, through T7EI and TIDE analysis, gRNAs #9 and #7 are the most efficient gRNAs targeting HLA-B (that is, corresponding to crRNA-B1 to crRNA-B2), and they are used as the gRNAs for the subsequent knock-out of HLA-B.

Therefore, HLA-A and HLA-B (AB dKO) can be efficiently knocked out simultaneously using the HLA-A and HLA-B gRNAs.

Example 5 Production of HLA-A/B Double Knockout Universal CAR-T Cells

Through the above gRNA screening experiments, TCR, β2M, HLA-A, and HLA-B were successfully knocked out individually or in combination using the preferred gRNAs. The corresponding variety of different CAR-T cells were obtained and tested to evaluate whether the various prepared CAR-T cells met the clinical requirements: that is, the T cells belong to a universal CAR-T (UCAR-T) cell that does not induce GVHD, and the T cells can effectively avoid being attacked and killed by NK cells.

Figure 12:
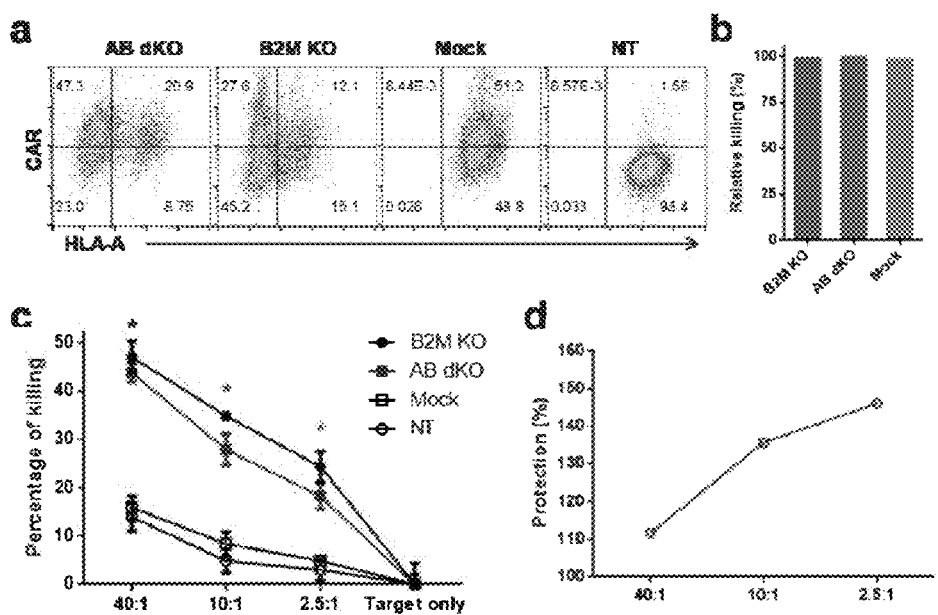
FIG. 12 shows that AB dKO CAR-T cells have stronger NK cell killer protection than β2M KO CAR-T.

The results are shown in FIG. 12. Using the knockout gRNAs of HLA-A, HLA-B, TRAC, and β2M obtained in Example 4, TCR and HLA-A were knocked out successfully in human primary T cells, and CD19 CAR was integrated into the T cell genome by lentiviral infection. Two universal CAR-T cells, AB dKO and β2M KO, were successfully obtained through these operations.

The Hela-CD19 cell line was then used to test the function of CD19 CAR. The Hela-CD19 killing by CAR-T was detected using RTCA.

The results are shown in FIG. 12b, and the function of CD19 CAR was not affected by the knockout of HLA-A/B.

It was tested whether the knockout of HLA-A/B achieved protection against NK killing for the universal CAR-T, compared with the knockout of β2M. The results are shown in FIG. 12c and FIG. 12d. NK92 cells killed both AB dKO and β2M KO cells, but the killing degree of AB dKO cells (both HLA-A and HLA-B were knocked out, while β2M was not knocked out) was significantly and unexpectedly weaker than that of β2M KO cells (β2M was knocked out, and neither HLA-A nor HLA-B was knocked out). In addition, CAR-T cells prepared by knocking out only HLA-A or only HLA-B are not easily killed by NK92 cells, but are easily killed by host T cells.

The above results show that compared with conventional knockout of β2M, universal CAR-T cells can be significantly protected by HLA-A and/or HLA-B knockout to a certain extent, of which double knockout of HLA-A and HLA-B is optimal in terms of comprehensive performance. It suggests that the universal CAR-T cells of the invention have a longer survival time and a longer time to function in the recipient.

Example 6 Culture of CART Cells 6.1 Cell Isolation and Activation

After the donor apheresis was obtained, density gradient centrifugation was performed using Histopaque-1077 (Sigma-Aldrich) to isolate monocytes from the donor apheresis. T cells were enriched. Using anti-CD3ζ/anti-CD28 conjugated magnetic beads, the T cells were activated, cultured and amplified.

X-vivo15 (containing 5% FBS, 2 mM L-glutamine, 1 mM sodium pyruvate, 300IU/ml rhIL2) was used as CART cell culture medium. All cells were cultured in an incubator at 37° C., 5% $CO_2$.

CD19-expressing cell lines comprised: Raji (Burkitt's lymphoma cell line (ATCC-CCL86); K562 cells (human erythroleukemic cell line (ATCC-CCL243)). Raji-ffluc cell line (obtained by screening fireflyluciferase Lentivirus infected Raji cells). All cells above were cultured in RPMI1640 medium. 293T (ATCC-CRL3216) was cultured in DMEM medium. All media were supplemented with 10% (v/v) fetal calf serum and 100 U/ml of avidin and streptomycin, 2 mM glutamine, and 1 mM sodium pyruvate.

6.2 Lentivirus infection

The isolated and purified primary T cells were infected with lentiviral vector at MOI (2-8) 2 days after activation. The cells were transferred to a cell culture flask, and cultured in an incubator at 37° C., 5% $CO_2$.

6.3 Electroporation

On the second day after virus infection, the virus were removed, and the cells needed for electroporation were collected and placed in a centrifuge tube. The cells were centrifuged at 300 g for 5 min, and washed twice with DPBS, and then resuspended with opti-mem to a cell density of $1-3 \times 10^8$/ml. The required amount of cas9/gRNA was calculated according to the density of the cells, each 30 ug/ml. The required Cas9 and gRNA were mixed in a ratio of 1:1. The mixture was incubated at room temperature for 10 minutes, then added to the electroporation buffer and mixed with the cells. Then the mixture was added to the electrode cup. The program EO-115 of 4D-Nucleofector System N (Lonza) electroporation system was selected to preform the electroporation. After the electroporation, the cells were resuspended to a cell density of $1-2 \times 10^6$/ml with the pre-warmed medium. The cells were transferred to corresponding culture dish and continue cultured in an incubator at 37° C., 5% $CO_2$.

6.4 Cell Proliferation and CAR Positive Proportion Detection

On the third day after infection, the number of cells and the proportion of CAR-positive cells were detected, that is, the CAR-positive proportion of T cells was detected. Negative screening was performed with CD3ζ/β2 m antibodies at the same time. Double-negative cells were required cells. The required cells were continued to be cultured in an incubator. Half of the medium was replaced every 2-3 days. After 14 days of culture, the cells can be frozen.

Example 7 Cytokine Release Assay

CD19 CAR-T cells and AB dKO CD19 CAR-T cells (that is, CD19 CAR-T cells in which both HLA-A and HLA-B were knocked out, while β2M was not knocked out) were mixed with tumor cells in a ratio of 1:1 and placed in RPMI medium. Each cell density was prepared as $1 \times 10^6$/ml. 100 ul of each CAR-T cells and tumor cells were placed in 96-well plates, and co-cultured overnight. The supernatant was collected and centrifuged. The release levels of cytokines IFN-γ and IL2 in supernatant were detected using Elisa kit (Biolegend).

The results showed that after being stimulated by target cells, CD19 CAR-T cells and AB dKO CD19 CAR-T cells can secrete a large amount of IFN-γ and IL-2, with no significant difference between the two groups.

Example 8 Killing of Cells In Vitro

The luciferase gene was transferred into target cells, and stable transfected cell lines were obtained after clone and screening. During the experiment, the luciferin substrate was added, and the luciferase reacts with luciferin to generate fluorescence. The intensity of the fluorescence can be measured to determine the activity of the luciferase. The survival rate of cells was detected and the killing effect of the CART cells was obtained.

The results showed that CD19 CAR-T cells and AB dKO CD19 CAR-T cells had a stronger target cell killing effect than the control T cells. There was no significant difference between CD19 CAR-T cells and AB dKO CD19 CAR-T cells.

Example 9 In vivo Pharmacodynamic Study 6-12 week old NOD-Prkdescid Il2rgnull (NPG) mice were selected and intraperitoneally injected with $2 \times 10^5$ Raji-ffluc cells, 50 μL DPBS and 50 μL matrigel matrix (Corning). Tumor graft load was detected after two days. The mice were divided into 4 groups with equivalent tumor burden. One day after grouping, 200 μL DPBS/mouse, $5 \times 10^6$ CD19 CAR-T cells/mouse, $5 \times 10^6$ CD19 CAR-T cells/mouse, $5 \times 10^6$ AB dKO CD19 CAR-T cells/mouse were injected, respectively. The tumor burden of the mice was assessed 7 days after CAR-T treatment. 3 mg d-fluorescein/mouse were injected intraperitoneally, and reacted for four minutes. A picture was taken using the Xenogen IVIS imaging system and expose for 30 seconds.

The results showed that the tumor burden of CD19 CAR-T cell group and AB dKO CD19 CAR-T cell group was significantly reduced, and there was no significant difference between the two groups.

Example 10 In Vivo GVHD Experiment

Before the experiment, mice were treated with systemic sublethal dose irradiation (175 cGy). T cells and AB dKO CD19 CAR-T cells were resuspended using FBS and injected into the thorax of the irradiated mice. GVHD symptoms in mice were evaluated using clinical standard tests, which were tested 2-3 times a week. Clinical indicators included weight loss, arch back, activity, fur texture, and skin integrity.

The results showed that mice injected with T cells with TCR not knocked out all developed GVHD and died, while the group injected with AB dKO CD19 CAR-T cell were not detected a GVHD response.

Example 11 In Vitro HVG Experiment

The irradiated AB dKO CD19 CAR-T cells and T cells were incubated with allogeneic T cells and NK cells overnight at 1:1 to detect cell apoptosis and cytokine release (IL-2, IFN-r).

The results showed that compared with the control group, AB dKO CD 19 CAR-T cells had almost no apoptosis, and the cytokine release was significantly lower than that of the T cell group.

All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A universal chimeric antigen receptor T cell (CAR-T cell) with the following characteristics:
   (a) the CAR-T cell expresses a chimeric antigen receptor (CAR), and the CAR targets a marker of tumor cells; and
   (b) HLA-A and HLA-B gene expression of the CAR-T cell is silenced using a CRISPR-Cas9 gene editing system, so that the binding of the HLA-A and/or the HLA-B to a TCR (T cell receptor) is inhibited, and endogenous β2 m gene of the CAR-T cell is expressed;
   wherein, the CRISPR-Cas9 system comprises a Cas9 protein and gRNAs comprising:
   a gRNA targeting HLA-a, having the nucleotide sequence of SEQ ID NO: 20 or SEQ ID NO: 23, and
   a gRNA targeting HLA-b, having the nucleotide sequence of SEQ ID NO: 26.

2. The CAR-T cell of claim 1, wherein the CAR-T cell expresses an exogenous ligand fragment or antibody fragment that binds to a killer-cell immunoglobulin-like receptor (KIR).

3. The CAR-T cell of claim 1, wherein the TCR gene expression of the CAR-T cell is silenced.

4. The CAR-T cell of claim 1, wherein the structure of the CAR is shown in formula I as below:

L1-scFv-H1-TM1-C-CD3ζ-K    (I)

wherein,
each "-" is independently a linker or peptide bond;
L1 is an optional signal peptide sequence;
scFv is an antigen binding domain;
H1 is an optional hinge region;
TM1 is a transmembrane domain;
C is a co-stimulatory signaling molecule;
CD3ζ is a cytoplasmic signaling sequence derived from CD3ζ;
K is an optional KIR ligand element.

5. A method for preparing the CAR-T cell of claim 1, comprising the following steps:
   (A) providing a T cell to be modified; and
   (B) modifying the T cell to express the CAR, and inhibiting the binding of HLA-A and/or HLA-B of the CAR-T cell to TCR, thereby obtaining the CAR-T cell of claim 1.

6. A preparation comprising the CAR-T cell of claim 1, and a pharmaceutically acceptable carrier, diluent or excipient.

7. A kit for preparing the CAR-T cell of claim 1 comprising a container and following components located in the container:
   (1) a first nucleic acid sequence comprising a first expression cassette for expressing the CAR;
   (2) a gRNA for silencing HLA-a comprising SEQ ID NO: 20 or SEQ ID NO: 23 and a gRNA for silencing HLA-b comprising SEQ ID NO: 26.

8. The CAR-T cell of claim 1, wherein the HLA-C gene expression of the CAR-T cell is not affected.

9. The CAR-T cell of claim 2, wherein the ligand fragment of the inhibitory receptor comprises a full-length HLA-C or an HLA-C fragment.

10. The CAR-T cell of claim 1, wherein the "binding of HLA-A and/or HLA-B to TCR is inhibited" means that HLA-A does not bind to the TCR or the ratio of binding amount A1 of the HLA-A of the CAR-T cell to the TCR to the binding amount A0 of a HLA-A of a normal T cell to the TCR (A1/A0) is ≤0.05, and/or HLA-B does not bind to the TCR or the ratio of binding amount B1 of the HLA-B of the CAR-T cell to the TCR to the binding amount B0 of a HLA-B of a normal T cell to TCR (B1/B0) is ≤0.05.

* * * * *

SEQUENCE LISTING

```
<160> NUMBER OF SEQ ID NOS: 40

<210> SEQ ID NO 1
<211> LENGTH: 1470
<212> TYPE: DNA
<213> ORGANISM: Artificial Sequence
<220> FEATURE:
<223> OTHER INFORMATION: CAR

<400> SEQUENCE: 1
atgcttctcc tggtgacaag ccttctgctc tgtgagttac cacacccagc attcctcctg      60
atcccagaca tccagatgac acagactaca tcctccctgt ctgcctctct gggagacaga     120
gtcaccatca gttgcagggc aagtcaggac attagtaaat atttaaattg gtatcagcag     180
aaaccagatg gaactgttaa actcctgatc taccatacat caagattaca ctcaggagtc     240
ccatcaaggt tcagtggcag tgggtctgga acagattatt ctctcaccat tagcaacctg     300
gagcaagaag atattgccac ttacttttgc caacagggta atacgcttcc gtacacgttc     360
ggagggggga ctaagttgga aataacaggc tccacctctg gatccggcaa gcccggatct     420
ggcgagggat ccaccaaggg cgaggtgaaa ctgcaggagt caggacctgg cctggtggcg     480
ccctcacaga gcctgtccgt cacatgcact gtctcagggg tctcattacc cgactatggt     540
gtaagctgga ttcgccagcc tccacgaaag ggtctggagt ggctgggagt aatatggggt     600
agtgaaacca catactataa ttcagctctc aaatccagac tgaccatcat caaggacaac     660
tccaagagcc aagttttctt aaaaatgaac agtctgcaaa ctgatgacac agccatttac     720
tactgtgcca acattatta ctacggtggt agctatgcta tggactactg gggtcaagga     780
acctcagtca ccgtctcctc agcggccgca attgaagtta tgtatcctcc tccttaccta     840
gacaatgaga agagcaatgg aaccattatc catgtgaaag gaaacaccct tgtccaagt      900 cccctatttc ccgaccttc taagcccttt tgggtgctgg tggtggttgg gggagtcctg      960
gcttgctata gcttgctagt aacagtggcc tttattattt tctgggtgag gagtaagagg     1020
agcaggctcc tgcacagtga ctacatgaac atgactcccc gccgccccgg gcccacccgc     1080
aagcattacc agccctatgc cccaccacgc gacttcgcag cctatcgctc cagagtgaag     1140
ttcagcagga gcgcagacgc ccccgcgtac cagcagggcc agaaccagct ctataacgag     1200
ctcaatctag gacgaagaga ggagtacgat gttttggaca gagacgtgg ccgggaccct      1260 gagatggggg gaaagccgag aaggaagaac cctcaggaag gcctgtacaa tgaactgcag     1320
```

```
aaagataaga tggcggaggc ctacagtgag attgggatga aaggcgagcg ccggaggggc    1380 aagggcacg atggccttta ccagggtctc agtacagcca ccaaggacac ctacgacgcc     1440
cttcacatgc aggccctgcc ccctcgctaa                                     1470
```

<210> SEQ ID NO 2
<211> LENGTH: 489
<212> TYPE: PRT
<213> ORGANISM: Artificial Sequence
<220> FEATURE:
<223> OTHER INFORMATION: CAR

<400> SEQUENCE: 2

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335
```

```
Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
            450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 3
<211> LENGTH: 109
<212> TYPE: PRT
<213> ORGANISM: Artificial Sequence
<220> FEATURE:
<223> OTHER INFORMATION: 1-7F9VL

<400> SEQUENCE: 3

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105

<210> SEQ ID NO 4
<211> LENGTH: 123
<212> TYPE: PRT
<213> ORGANISM: Artificial Sequence
<220> FEATURE:
<223> OTHER INFORMATION: 1-7F9VH

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
```

35                  40                  45
Gly Gly Phe Ile Pro Ile Phe Gly Ala Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 5
<211> LENGTH: 80
<212> TYPE: DNA
<213> ORGANISM: Artificial Sequence
<220> FEATURE:
<223> OTHER INFORMATION: crRNA

<400> SEQUENCE: 5
gttttagagc tagaaatagc aagttaaaat aaggctagtc cgttatcaac ttgaaaaagt      60
ggcaccgagt cggtgctttt                                                  80

<210> SEQ ID NO 6
<211> LENGTH: 20
<212> TYPE: DNA
<213> ORGANISM: Artificial Sequence
<220> FEATURE:
<223> OTHER INFORMATION: crRNA

<400> SEQUENCE: 6
tggatttaga gtctctcagc                                                  20

<210> SEQ ID NO 7
<211> LENGTH: 20
<212> TYPE: DNA
<213> ORGANISM: Artificial Sequence
<220> FEATURE:
<223> OTHER INFORMATION: crRNA

<400> SEQUENCE: 7
ttcggaaccc aatcactgac                                                  20

<210> SEQ ID NO 8
<211> LENGTH: 20
<212> TYPE: DNA
<213> ORGANISM: Artificial Sequence
<220> FEATURE:
<223> OTHER INFORMATION: crRNA

<400> SEQUENCE: 8
aagttcctgt gatgtcaagc                                                  20

<210> SEQ ID NO 9
<211> LENGTH: 20
<212> TYPE: DNA
<213> ORGANISM: Artificial Sequence
<220> FEATURE:
<223> OTHER INFORMATION: crRNA

<400> SEQUENCE: 9
tcagggttct ggatatctgt                                                  20

```
<210> SEQ ID NO 10
<211> LENGTH: 20
<212> TYPE: DNA
<213> ORGANISM: Artificial Sequence
<220> FEATURE:
<223> OTHER INFORMATION: crRNA

<400> SEQUENCE: 10
ctggagggcc ctgagcagag                                               20

<210> SEQ ID NO 11
<211> LENGTH: 20
<212> TYPE: DNA
<213> ORGANISM: Artificial Sequence
<220> FEATURE:
<223> OTHER INFORMATION: crRNA

<400> SEQUENCE: 11
gagcagcagg caggttaggc                                               20

<210> SEQ ID NO 12
<211> LENGTH: 20
<212> TYPE: DNA
<213> ORGANISM: Artificial Sequence
<220> FEATURE:
<223> OTHER INFORMATION: crRNA

<400> SEQUENCE: 12
cgtgagtaaa cctgaatctt                                               20

<210> SEQ ID NO 13
<211> LENGTH: 20
<212> TYPE: DNA
<213> ORGANISM: Artificial Sequence
<220> FEATURE:
<223> OTHER INFORMATION: crRNA

<400> SEQUENCE: 13
tataagtgga ggcgtcgcgc                                               20

<210> SEQ ID NO 14
<211> LENGTH: 20
<212> TYPE: DNA
<213> ORGANISM: Artificial Sequence
<220> FEATURE:
<223> OTHER INFORMATION: crRNA

<400> SEQUENCE: 14
ggccgagatg tctcgctccg                                               20

<210> SEQ ID NO 15
<211> LENGTH: 20
<212> TYPE: DNA
<213> ORGANISM: Artificial Sequence
<220> FEATURE:
<223> OTHER INFORMATION: crRNA

<400> SEQUENCE: 15
aagtcaactt caatgtcgga                                               20

<210> SEQ ID NO 16
<211> LENGTH: 20
<212> TYPE: DNA
<213> ORGANISM: Artificial Sequence
<220> FEATURE:
<223> OTHER INFORMATION: crRNA
```

-continued

```
<400> SEQUENCE: 16
actcacgctg gatagcctcc                                               20

<210> SEQ ID NO 17
<211> LENGTH: 20
<212> TYPE: DNA
<213> ORGANISM: Artificial Sequence
<220> FEATURE:
<223> OTHER INFORMATION: crRNA

<400> SEQUENCE: 17
ggccacggag cgagacatct                                               20

<210> SEQ ID NO 18
<211> LENGTH: 20
<212> TYPE: DNA
<213> ORGANISM: Artificial Sequence
<220> FEATURE:
<223> OTHER INFORMATION: crRNA

<400> SEQUENCE: 18
cgcgagcaca gctaaggcca                                               20

<210> SEQ ID NO 19
<211> LENGTH: 20
<212> TYPE: DNA
<213> ORGANISM: Artificial Sequence
<220> FEATURE:
<223> OTHER INFORMATION: crRNA

<400> SEQUENCE: 19
gagtagcgcg agcacagcta                                               20

<210> SEQ ID NO 20
<211> LENGTH: 20
<212> TYPE: DNA
<213> ORGANISM: Artificial Sequence
<220> FEATURE:
<223> OTHER INFORMATION: crRNA

<400> SEQUENCE: 20
ccctcctcct gctactctcg                                               20

<210> SEQ ID NO 21
<211> LENGTH: 20
<212> TYPE: DNA
<213> ORGANISM: Artificial Sequence
<220> FEATURE:
<223> OTHER INFORMATION: crRNA

<400> SEQUENCE: 21
gcgcccgcgg ctccatcctc                                               20

<210> SEQ ID NO 22
<211> LENGTH: 20
<212> TYPE: DNA
<213> ORGANISM: Artificial Sequence
<220> FEATURE:
<223> OTHER INFORMATION: crRNA

<400> SEQUENCE: 22
ccagggcccc cgagagtagc                                               20

<210> SEQ ID NO 23
```

<210> SEQ ID NO 23
<211> LENGTH: 20
<212> TYPE: DNA
<213> ORGANISM: Artificial Sequence
<220> FEATURE:
<223> OTHER INFORMATION: crRNA

<400> SEQUENCE: 23
cactcggtca gtctgtgact                                       20

<210> SEQ ID NO 24
<211> LENGTH: 20
<212> TYPE: DNA
<213> ORGANISM: Artificial Sequence
<220> FEATURE:
<223> OTHER INFORMATION: crRNA

<400> SEQUENCE: 24
gataatgtat ggctgcgacg                                       20

<210> SEQ ID NO 25
<211> LENGTH: 20
<212> TYPE: DNA
<213> ORGANISM: Artificial Sequence
<220> FEATURE:
<223> OTHER INFORMATION: crRNA

<400> SEQUENCE: 25
acagactgac cgagtggacc                                       20

<210> SEQ ID NO 26
<211> LENGTH: 20
<212> TYPE: DNA
<213> ORGANISM: Artificial Sequence
<220> FEATURE:
<223> OTHER INFORMATION: crRNA

<400> SEQUENCE: 26
ggaggtgtag aaatacctca                                       20

<210> SEQ ID NO 27
<211> LENGTH: 20
<212> TYPE: DNA
<213> ORGANISM: Artificial Sequence
<220> FEATURE:
<223> OTHER INFORMATION: crRNA

<400> SEQUENCE: 27
atttctacac ctccgtgtcc                                       20

<210> SEQ ID NO 28
<211> LENGTH: 20
<212> TYPE: DNA
<213> ORGANISM: Artificial Sequence
<220> FEATURE:
<223> OTHER INFORMATION: crRNA

<400> SEQUENCE: 28
tggacgacac ccagttcgtg                                       20

<210> SEQ ID NO 29
<211> LENGTH: 20
<212> TYPE: DNA
<213> ORGANISM: Artificial Sequence
<220> FEATURE:
<223> OTHER INFORMATION: crRNA

<400> SEQUENCE: 29
agcagcagga ggacggttcg                                                    20

<210> SEQ ID NO 30
<211> LENGTH: 20
<212> TYPE: DNA
<213> ORGANISM: Artificial Sequence
<220> FEATURE:
<223> OTHER INFORMATION: crRNA

<400> SEQUENCE: 30
cgctgtcgaa cctcacgaac                                                    20

<210> SEQ ID NO 31
<211> LENGTH: 20
<212> TYPE: DNA
<213> ORGANISM: Artificial Sequence
<220> FEATURE:
<223> OTHER INFORMATION: crRNA

<400> SEQUENCE: 31
gagcatgtac ggctgcgacg                                                    20

<210> SEQ ID NO 32
<211> LENGTH: 34
<212> TYPE: PRT
<213> ORGANISM: Artificial Sequence
<220> FEATURE:
<223> OTHER INFORMATION: Synthetic

<400> SEQUENCE: 32

Ser Glu Glu Gly Lys Phe Lys Gly Pro Met Met Gln Asp Leu Ala Gly
1               5                   10                  15

Leu Tyr Glu Lys Pro Ser Arg Ser Ser Tyr Asp Phe Arg Asp Ser Pro
            20                  25                  30

Tyr Glu

<210> SEQ ID NO 33
<211> LENGTH: 35
<212> TYPE: PRT
<213> ORGANISM: Artificial Sequence
<220> FEATURE:
<223> OTHER INFORMATION: Syntheitc
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid
<220> FEATURE:
<221> NAME/KEY: misc_feature
<222> LOCATION: (18)..(27)
<223> OTHER INFORMATION: Xaa can be any naturally occurring amino acid
<220> FEATURE:
<221> NAME/KEY: misc_feature
<222> LOCATION: (29)..(35)
<223> OTHER INFORMATION: Xaa can be any naturally occurring amino acid

<400> SEQUENCE: 33

```
Xaa Xaa Xaa Xaa Met Xaa Asn Ser Arg Xaa Thr Xaa Xaa Xaa Xaa
1               5                   10                  15

Leu Xaa Xaa Xaa Xaa Xaa Xaa Xaa Xaa Xaa His Xaa Xaa Xaa
            20                  25              30

Xaa Xaa Xaa
        35
```

<210> SEQ ID NO 34
<211> LENGTH: 32
<212> TYPE: PRT
<213> ORGANISM: Artificial Sequence
<220> FEATURE:
<223> OTHER INFORMATION: Syntheitc
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(27)
<223> OTHER INFORMATION: Xaa can be any naturally occurring amino acid
<220> FEATURE:
<221> NAME/KEY: misc_feature
<222> LOCATION: (29)..(32)
<223> OTHER INFORMATION: Xaa can be any naturally occurring amino acid

<400> SEQUENCE: 34

```
Xaa Gly Xaa Xaa Ile Ser Xaa Xaa Xaa Xaa Leu Ala Xaa Pro Xaa
1               5                   10                  15

Xaa Xaa Xaa Xaa Xaa Xaa Xaa Xaa Xaa Xaa His Xaa Xaa Xaa Xaa
            20                  25              30
```

<210> SEQ ID NO 35
<211> LENGTH: 66
<212> TYPE: PRT
<213> ORGANISM: Artificial Sequence
<220> FEATURE:
<223> OTHER INFORMATION: Synthetic

<400> SEQUENCE: 35

```
Glu Gly Pro Glu Tyr Trp Asp Arg Glu Thr Gln Lys Tyr Lys Arg Gln
1               5                   10                  15

Ala Gln Thr Asp Arg Val Ser Leu Arg Asn Leu Arg Gly Tyr Tyr Asn
            20                  25                  30

Gln Ser Glu Ala Gln Ile Thr Gln Arg Lys Trp Glu Ala Ala Arg Glu
        35                  40                  45

Ala Glu Gln Leu Arg Ala Tyr Leu Glu Gly Leu Cys Val Glu Trp Leu
    50                  55                  60

Arg Arg
65
```

<210> SEQ ID NO 36
<211> LENGTH: 66
<212> TYPE: PRT
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(18)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(35)
<223> OTHER INFORMATION: Xaa can be any naturally occurring amino acid
<220> FEATURE:
<221> NAME/KEY: misc_feature
<222> LOCATION: (37)..(51)
<223> OTHER INFORMATION: Xaa can be any naturally occurring amino acid
<220> FEATURE:
<221> NAME/KEY: misc_feature
<222> LOCATION: (53)..(58)
<223> OTHER INFORMATION: Xaa can be any naturally occurring amino acid
<220> FEATURE:
<221> NAME/KEY: misc_feature
<222> LOCATION: (60)..(66)
<223> OTHER INFORMATION: Xaa can be any naturally occurring amino acid

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Ala Xaa Xaa Xaa Asn Xaa Lys Xaa Xaa Xaa Xaa Xaa Xaa Xaa
            20                  25                  30

Xaa Xaa Xaa Asp Xaa Xaa Xaa Xaa Xaa Xaa Xaa Xaa Xaa Xaa Xaa Xaa
        35                  40                  45

Xaa Xaa Xaa Arg Xaa Xaa Xaa Xaa Xaa Thr Xaa Xaa Xaa Xaa Xaa Xaa
    50                  55                  60

Xaa Xaa
65

<210> SEQ ID NO 37
<211> LENGTH: 65
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(46)
<223> OTHER INFORMATION: Xaa can be any naturally occurring amino acid
```

```
<220> FEATURE:
<221> NAME/KEY: misc_feature
<222> LOCATION: (48)..(57)
<223> OTHER INFORMATION: Xaa can be any naturally occurring amino acid
<220> FEATURE:
<221> NAME/KEY: misc_feature
<222> LOCATION: (59)..(65)
<223> OTHER INFORMATION: Xaa can be any naturally occurring amino acid

<400> SEQUENCE: 37

Xaa Xaa Xaa Xaa Xaa Xaa Xaa Xaa Xaa Xaa Xaa Ile Cys Xaa Ala Lys
1               5                   10                  15

Xaa Xaa Xaa Xaa Xaa Glu Asp Xaa Thr Xaa Leu Arg Xaa Xaa Xaa Xaa
            20                  25                  30

Xaa Xaa Xaa Xaa Xaa Xaa Xaa Xaa Xaa Xaa Xaa Xaa Xaa Val Xaa
        35                  40                  45

Xaa Xaa Xaa Xaa Xaa Xaa Xaa Xaa Xaa Glu Xaa Xaa Xaa Xaa Xaa Xaa
    50                  55                  60

Xaa
65

<210> SEQ ID NO 38
<211> LENGTH: 66
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(21)
<223> OTHER INFORMATION: Xaa can be any naturally occurring amino acid
<220> FEATURE:
<221> NAME/KEY: misc_feature
<222> LOCATION: (23)..(47)
<223> OTHER INFORMATION: Xaa can be any naturally occurring amino acid
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: misc_feature
<222> LOCATION: (53)..(58)
<223> OTHER INFORMATION: Xaa can be any naturally occurring amino acid
<220> FEATURE:
<221> NAME/KEY: misc_feature
<222> LOCATION: (60)..(66)
<223> OTHER INFORMATION: Xaa can be any naturally occurring amino acid

<400> SEQUENCE: 38

Xaa Xaa Xaa Xaa Xaa Xaa Xaa Xaa Asn Xaa Xaa Ile Phe Xaa Thr Asn
1               5                   10                  15

Xaa Xaa Xaa Xaa Xaa Glu Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Val
        35                  40                  45

Xaa Xaa Xaa Asp Xaa Xaa Xaa Xaa Xaa Xaa Thr Xaa Xaa Xaa Xaa Xaa
    50                  55                  60
```

Xaa Xaa
65

<210> SEQ ID NO 39
<211> LENGTH: 66
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (42)..(46)
<223> OTHER INFORMATION: Xaa can be any naturally occurring amino acid
<220> FEATURE:
<221> NAME/KEY: misc_feature
<222> LOCATION: (49)..(58)
<223> OTHER INFORMATION: Xaa can be any naturally occurring amino acid
<220> FEATURE:
<221> NAME/KEY: misc_feature
<222> LOCATION: (60)..(66)
<223> OTHER INFORMATION: Xaa can be any naturally occurring amino acid

<400> SEQUENCE: 39

Xaa Xaa Xaa Xaa Xaa Xaa Xaa Gly Xaa Xaa Arg Xaa Val Xaa Ala His
1               5                   10                  15

Ser Xaa Xaa His Xaa Xaa Asp Xaa Gly Thr Xaa Xaa Xaa Xaa Xaa Xaa
            20                  25                  30

Xaa Xaa Xaa Xaa Xaa Thr Xaa Lys His Xaa Xaa Xaa Xaa Xaa His Val
        35                  40                  45

Xaa Xaa Xaa Xaa Xaa Xaa Xaa Xaa Xaa Xaa Thr Xaa Xaa Xaa Xaa Xaa
    50                  55                  60

Xaa Xaa
65

<210> SEQ ID NO 40

```
<211> LENGTH: 66
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (8)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(34)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (42)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: misc_feature
<222> LOCATION: (53)..(58)
<223> OTHER INFORMATION: Xaa can be any naturally occurring amino acid
<220> FEATURE:
<221> NAME/KEY: misc_feature
<222> LOCATION: (60)..(66)
<223> OTHER INFORMATION: Xaa can be any naturally occurring amino acid

<400> SEQUENCE: 40

Xaa Xaa Xaa Xaa Xaa Xaa Glu Xaa Xaa Xaa Xaa Xaa Ala Xaa Gly Asn
1               5                   10                  15

Glu Xaa Ser Phe Xaa Xaa Asp Xaa Xaa Thr Xaa Leu Xaa Xaa Xaa Xaa
            20                  25                  30

Xaa Xaa Lys Gly Leu Xaa Xaa Lys His Xaa Xaa Xaa Xaa Gln Xaa Gly
        35                  40                  45

Xaa Xaa Xaa Arg Xaa Xaa Xaa Xaa Xaa Thr Xaa Xaa Xaa Xaa Xaa
    50                  55                  60

Xaa Xaa
65
```